United States Patent [19]
Kofod et al.

[11] Patent Number: 5,885,819
[45] Date of Patent: Mar. 23, 1999

[54] ENZYME WITH XYLANASE ACTIVITY

[75] Inventors: Lene Venke Kofod, Ugerloese; Markus Sakari Kauppinen, Copenhagen; Stephan Christgau, Vedbaek; Hans Peter Heldt-Hansen, Virum; Henrik Dalbøge, Esbjerg; Lene Nonboe Andersen, Birkerød; Joan Qi Si, Klampenborg; Tina Sejersgård Jacobsen, Copenhagen; Niels Munk, Frederiksberg; Anette Müllertz, Charlottenlund, all of Denmark

[73] Assignee: Novo Nordisk A/S, Bagsvaerd, Denmark

[21] Appl. No.: 902,655

[22] Filed: Jul. 30, 1997

Related U.S. Application Data

[62] Division of Ser. No. 507,431, filed as PCT/DK94/00088, filed Mar. 2, 1994, Pat. No. 5,693,518.

[30] Foreign Application Priority Data

Mar. 10, 1993 [DK] Denmark .................................. 0268/93
Oct. 14, 1993 [DK] Denmark .................................. 1151/93

[51] Int. Cl.$^6$ .............................. C12N 9/24; C12N 1/22; C12N 15/00; C07H 21/04
[52] U.S. Cl. ................. 435/200; 435/252.3; 435/254.11; 435/254.2; 435/254.3; 435/320.1; 536/23.2; 536/23.74
[58] Field of Search ................................ 435/200, 252.3, 435/254.11, 254.2, 254.3, 320.1; 536/23.2, 23.74

[56] References Cited

U.S. PATENT DOCUMENTS 5,610,046  3/1997  Van Ooyen et al. ................... 435/200

FOREIGN PATENT DOCUMENTS

| 0 463 706 A1 | 7/1991 | European Pat. Off. . |
| WO 91/17244 | 11/1991 | WIPO . |
| WO 91/19782 | 12/1991 | WIPO . |
| WO 92/01793 | 2/1992 | WIPO . |
| WO 92/06209 | 4/1992 | WIPO . |
| WO 92/17573 | 10/1992 | WIPO . |
| WO 93/03155 | 2/1993 | WIPO . |
| WO 93/12237 | 6/1993 | WIPO . |

OTHER PUBLICATIONS

Ito et al. "Cloning sequenceing of the xynA gene encoding xylanase A of Aspergillus kawachii" Biosci. Biotechnol. Biochem. 56(6), 906–912, 1992.

Graff "Structure and regulation of an Aspergillus xylanase gene" Xylans and Xylanases, edited by Vissar et al., Elsevier Science Publishers B.V., pp. 235–246, 1992.

Paice et al., J. of Wood Chem. and Tech., vol. 4 (2), pp. 187–198 (1984).

Pommier et al., Tappi J., pp. 187–191,(1989).

Senior et al., Biotech. Letters, vol. 10, No. 12, pp. 907–912 (1988).

Shei et al., Biotech. and Bioeng., vol. XXVII, pp. 533–538 (1984).

Murao et al., J. Ferment Tech., vol. 57, No. 3, pp. 151–156 (1979).

Kiyoshi et al., Biosci. Biotech. Biochem., vol. 56 (6), pp. 906–912 (1992).

Haas et al., Biochimica et Biophysica Acta, 1117, pp. 279–286 (1992).

Grépinet et al., J. of Bacteriology 170, pp. 4576–4581, 1988.

Grépinet et al., J. of Bacteriology 170, pp. 4582–4588, (1988).

Shareck et al., Gene, vol. 197, pp. 75–82 (1991).

Ito et al., Biosci. Biotech., Biochem., vol. 56 (8), pp. 1338–1340 (1992).

Detroy, R.W, CRC Press, Organic Chemicals from Biomass, pp. 19–43, (1981).

*Primary Examiner*—Robert A. Wax
*Assistant Examiner*—Nashaat T. Nashed
*Attorney, Agent, or Firm*—Steve T. Zelson, Esq.; Cheryl H. Agris, Esq.

[57] ABSTRACT

An enzyme exhibiting xylanase activity, which enzyme is immunologically reactive with an antibody raised against a purified xylanase derived from *Aspergillus aculeatus*, CBS 101.43. The enzyme may be used for degrading plant cell wall components e.g. in the preparation of feed, in baking, in the paper and pulp industry and in connection with separation of wheat into starch and gluten.

44 Claims, 10 Drawing Sheets

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 1273 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(68..1048, 1052..1084, 1088..1093, 1097..1102, 1106..1273)

( x i ) SEQUENCE DESCRIPTION: SEQ ID NO:1:

```
CATCAACATT CATTCATTCA TTTAATTCAT TCCTCAAGCT CAAGAGCAGT CATCCCTTCT        60

TTCCAAC ATG GTT CAA ATC AAA GCA GCT GCT CTG GCT GTC CTT TTC GCC        109
        Met Val Gln Ile Lys Ala Ala Ala Leu Ala Val Leu Phe Ala
        1           5                       10

AGC AAT GTG CTC TCC AAC CCC ATC GAG CCC CGC CAG GCC TCG GTG AGC        157
Ser Asn Val Leu Ser Asn Pro Ile Glu Pro Arg Gln Ala Ser Val Ser
15              20                  25                          30

ATC GAT GCC AAA TTC AAG GCG CAC GGC AAG AAG TAC CTG GGC ACC ATC        205
Ile Asp Ala Lys Phe Lys Ala His Gly Lys Lys Tyr Leu Gly Thr Ile
                35                  40                      45

GGC GAC CAG TAC ACT CTC AAC AAG AAC GCA AAG ACC CCG GCG ATC ATC        253
Gly Asp Gln Tyr Thr Leu Asn Lys Asn Ala Lys Thr Pro Ala Ile Ile
            50                  55                  60

AAG GCC GAC TTT GGC CAG CTG ACT CCG GAG AAC AGC ATG AAG TGG GAT        301
Lys Ala Asp Phe Gly Gln Leu Thr Pro Glu Asn Ser Met Lys Trp Asp
            65              70                  75

GCT ACT GAG CCC AAC CGA GGA CAG TTC TCC TTC TCG GGG TCG GAT TAC        349
Ala Thr Glu Pro Asn Arg Gly Gln Phe Ser Phe Ser Gly Ser Asp Tyr
        80              85                  90

CTG GTC AAC TTC GCC CAG TCT AAC GGA AAG CTG ATC CGT GGC CAC ACT        397
Leu Val Asn Phe Ala Gln Ser Asn Gly Lys Leu Ile Arg Gly His Thr
95              100                 105                     110

CTC GTC TGG CAC TCA CAG CTC CCG TCC TGG GTG CAG TCC ATC TCC GAT        445
Leu Val Trp His Ser Gln Leu Pro Ser Trp Val Gln Ser Ile Ser Asp
                115                 120                 125

AAG AAC ACC CTG ATC CAA GTC ATG CAG AAT CAC ATC ACC ACC GTG ATG        493
Lys Asn Thr Leu Ile Gln Val Met Gln Asn His Ile Thr Thr Val Met
            130                 135                 140

CAG CGC TAC AAG GGC AAG GTC TAC GCC TGG GAC GTT GTC AAT GAG ATC        541
Gln Arg Tyr Lys Gly Lys Val Tyr Ala Trp Asp Val Val Asn Glu Ile
        145                 150                 155

TTC AAC GAG GAT GGC TCT CTT TGC CAG AGC CAC TTC TAC AAC GTC ATC        589
Phe Asn Glu Asp Gly Ser Leu Cys Gln Ser His Phe Tyr Asn Val Ile
    160                 165                 170

GGT GAG GAC TAT GTG CGC ATC GCT TTC GAG ACC GCT CGC GCG GTG GAT        637
Gly Glu Asp Tyr Val Arg Ile Ala Phe Glu Thr Ala Arg Ala Val Asp
175                 180                 185                 190

CCC AAC GCC AAG CTT TAC ATA AAC GAC TAC AAC CTG GAT TCC GCC TCG        685
Pro Asn Ala Lys Leu Tyr Ile Asn Asp Tyr Asn Leu Asp Ser Ala Ser
                195                 200                 205

TAC CCG AAA CTG ACC GGC CTG GTC AAC CAC GTC AAG AAG TGG GTC GCA        733
Tyr Pro Lys Leu Thr Gly Leu Val Asn His Val Lys Lys Trp Val Ala
                210                 215                 220

GCT GGC GTC CCC ATC GAC GGA ATT GGT TCC CAA ACC CAC CTG AGC GCG        781
Ala Gly Val Pro Ile Asp Gly Ile Gly Ser Gln Thr His Leu Ser Ala
            225                 230                 235

GGT GCC GGT GCT GCC GTC TCA GGA GCT CTC AAC GCT CTC GCT GGT GCA        829
Gly Ala Gly Ala Ala Val Ser Gly Ala Leu Asn Ala Leu Ala Gly Ala
        240                 245                 250

GGC ACC AAG GAG GTC GCT ATT ACC GAG CTC GAC ATC GCT GGC GCC AGC        877
Gly Thr Lys Glu Val Ala Ile Thr Glu Leu Asp Ile Ala Gly Ala Ser
255                 260                 265                 270

TCC ACC GAC TAC GTG AAC GTC GTC AAG GCG TGT CTG AAC CAG CCC AAG        925
Ser Thr Asp Tyr Val Asn Val Val Lys Ala Cys Leu Asn Gln Pro Lys
                275                 280                 285

TGC GTC GGT ATC ACC GTC TGG GGA AGT TCT GAC CCC GAC TCG TGG CGC        973
Cys Val Gly Ile Thr Val Trp Gly Ser Ser Asp Pro Asp Ser Trp Arg
            290                 295                 300

TCC AGC TCC AGC CCT CTG CTC TTC GAC AGC AAC TAC AAC CCC AAG GCT       1021
```

| Ser | Ser | Ser | Ser | Pro | Leu | Leu | Phe | Asp | Ser | Asn | Tyr | Asn | Pro | Lys | Ala | |
|---|---|---|---|---|---|---|---|---|---|---|---|---|---|---|---|---|
| | | 305 | | | | | 310 | | | | | 315 | | | | |

| GCT | TAT | ACC | GCT | ATT | GCG | AAC | GCT | CTC | TAG | TGG | TCG | TCT | CTA | TCA | CTG | 1069 |
|---|---|---|---|---|---|---|---|---|---|---|---|---|---|---|---|---|
| Ala | Tyr | Thr | Ala | Ile | Ala | Asn | Ala | Leu | | Trp | Ser | Ser | Leu | Ser | Leu | |
| | 320 | | | | | 325 | | | | | | 330 | | | | |

| GTA | AAG | CTC | GCA | GCT | TAA | TCT | CGG | TGA | ATC | CAG | TGA | CTG | GAA | TGT | CGT | 1117 |
|---|---|---|---|---|---|---|---|---|---|---|---|---|---|---|---|---|
| Val | Lys | Leu | Ala | Ala | | Ser | Arg | | Ile | Gln | | Leu | Glu | Cys | Arg | |
| | 335 | | | | | | 340 | | | | | | | 345 | | |

| CGT | GAT | CGT | AGG | ATG | AAT | ACT | CGG | GGC | TTG | CGG | GTT | GCT | TTT | TCT | GTA | 1165 |
|---|---|---|---|---|---|---|---|---|---|---|---|---|---|---|---|---|
| Arg | Asp | Arg | Arg | Met | Asn | Thr | Arg | Gly | Leu | Arg | Val | Ala | Phe | Ser | Val | |
| | | | 350 | | | | | 355 | | | | | 360 | | | |

| TTT | TCA | CCT | GAA | GTC | ATC | ATT | ATG | TTG | CTG | AAC | CTT | CCT | CTT | CTC | TTA | 1213 |
|---|---|---|---|---|---|---|---|---|---|---|---|---|---|---|---|---|
| Phe | Ser | Pro | Glu | Val | Ile | Ile | Met | Leu | Leu | Asn | Leu | Pro | Leu | Leu | Leu | |
| | | 365 | | | | | 370 | | | | | 375 | | | | |

| TTG | ATC | AAT | GGT | GAG | CAT | CGT | TTT | ATT | TAT | AAA | AAA | AAA | AAA | AAA | AAA | 1261 |
|---|---|---|---|---|---|---|---|---|---|---|---|---|---|---|---|---|
| Leu | Ile | Asn | Gly | Glu | His | Arg | Phe | Ile | Tyr | Lys | Lys | Lys | Lys | Lys | Lys | |
| | 380 | | | | | 385 | | | | | 390 | | | | | |

| AAA | AAA | AAA | AAA | | | | | | | | | | | | | 1273 |
|---|---|---|---|---|---|---|---|---|---|---|---|---|---|---|---|---|
| Lys | Lys | Lys | Lys | | | | | | | | | | | | | |
| 395 | | | | | | | | | | | | | | | | |

( 2 ) INFORMATION FOR SEQ ID NO:2:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Val | Gln | Ile | Lys | Ala | Ala | Ala | Leu | Ala | Val | Leu | Phe | Ala | Ser | Asn |
|---|---|---|---|---|---|---|---|---|---|---|---|---|---|---|---|
| 1 | | | | 5 | | | | | 10 | | | | | 15 | |

| Val | Leu | Ser | Asn | Pro | Ile | Glu | Pro | Arg | Gln | Ala | Ser | Val | Ser | Ile | Asp |
|---|---|---|---|---|---|---|---|---|---|---|---|---|---|---|---|
| | | | 20 | | | | | 25 | | | | | 30 | | |

| Ala | Lys | Phe | Lys | Ala | His | Gly | Lys | Lys | Tyr | Leu | Gly | Thr | Ile | Gly | Asp |
|---|---|---|---|---|---|---|---|---|---|---|---|---|---|---|---|
| | | 35 | | | | | 40 | | | | | 45 | | | |

| Gln | Tyr | Thr | Leu | Asn | Lys | Asn | Ala | Lys | Thr | Pro | Ala | Ile | Ile | Lys | Ala |
|---|---|---|---|---|---|---|---|---|---|---|---|---|---|---|---|
| | 50 | | | | | 55 | | | | | 60 | | | | |

| Asp | Phe | Gly | Gln | Leu | Thr | Pro | Glu | Asn | Ser | Met | Lys | Trp | Asp | Ala | Thr |
|---|---|---|---|---|---|---|---|---|---|---|---|---|---|---|---|
| 65 | | | | | 70 | | | | | 75 | | | | | 80 |

| Glu | Pro | Asn | Arg | Gly | Gln | Phe | Ser | Phe | Ser | Gly | Ser | Asp | Tyr | Leu | Val |
|---|---|---|---|---|---|---|---|---|---|---|---|---|---|---|---|
| | | | | 85 | | | | | 90 | | | | | 95 | |

| Asn | Phe | Ala | Gln | Ser | Asn | Gly | Lys | Leu | Ile | Arg | Gly | His | Thr | Leu | Val |
|---|---|---|---|---|---|---|---|---|---|---|---|---|---|---|---|
| | | | | 100 | | | | | 105 | | | | | 110 | |

| Trp | His | Ser | Gln | Leu | Pro | Ser | Trp | Val | Gln | Ser | Ile | Ser | Asp | Lys | Asn |
|---|---|---|---|---|---|---|---|---|---|---|---|---|---|---|---|
| | | 115 | | | | | 120 | | | | | 125 | | | |

| Thr | Leu | Ile | Gln | Val | Met | Gln | Asn | His | Ile | Thr | Thr | Val | Met | Gln | Arg |
|---|---|---|---|---|---|---|---|---|---|---|---|---|---|---|---|
| | 130 | | | | | 135 | | | | | 140 | | | | |

| Tyr | Lys | Gly | Lys | Val | Tyr | Ala | Trp | Asp | Val | Val | Asn | Glu | Ile | Phe | Asn |
|---|---|---|---|---|---|---|---|---|---|---|---|---|---|---|---|
| 145 | | | | | 150 | | | | | 155 | | | | | 160 |

| Glu | Asp | Gly | Ser | Leu | Cys | Gln | Ser | His | Phe | Tyr | Asn | Val | Ile | Gly | Glu |
|---|---|---|---|---|---|---|---|---|---|---|---|---|---|---|---|
| | | | | 165 | | | | | 170 | | | | | 175 | |

| Asp | Tyr | Val | Arg | Ile | Ala | Phe | Glu | Thr | Ala | Arg | Ala | Val | Asp | Pro | Asn |
|---|---|---|---|---|---|---|---|---|---|---|---|---|---|---|---|
| | | | 180 | | | | | 185 | | | | | 190 | | |

| Ala | Lys | Leu | Tyr | Ile | Asn | Asp | Tyr | Asn | Leu | Asp | Ser | Ala | Ser | Tyr | Pro |
|---|---|---|---|---|---|---|---|---|---|---|---|---|---|---|---|
| | | 195 | | | | | 200 | | | | | 205 | | | |

| Lys | Leu | Thr | Gly | Leu | Val | Asn | His | Val | Lys | Lys | Trp | Val | Ala | Ala | Gly |
|---|---|---|---|---|---|---|---|---|---|---|---|---|---|---|---|
| | 210 | | | | | 215 | | | | | 220 | | | | |

| | | | | | | | | | | | | | | | | |
|---|---|---|---|---|---|---|---|---|---|---|---|---|---|---|---|---|
| Val | Pro | Ile | Asp | Gly | Ile | Gly | Ser | Gln | Thr | His | Leu | Ser | Ala | Gly | Ala | |
| 225 | | | | 230 | | | | | 235 | | | | | | 240 | |
| Gly | Ala | Ala | Val | Ser | Gly | Ala | Leu | Asn | Ala | Leu | Ala | Gly | Ala | Gly | Thr | |
| | | | | 245 | | | | 250 | | | | | | 255 | | |
| Lys | Glu | Val | Ala | Ile | Thr | Glu | Leu | Asp | Ile | Ala | Gly | Ala | Ser | Ser | Thr | |
| | | | 260 | | | | | 265 | | | | | 270 | | | |
| Asp | Tyr | Val | Asn | Val | Val | Lys | Ala | Cys | Leu | Asn | Gln | Pro | Lys | Cys | Val | |
| | | 275 | | | | | 280 | | | | | 285 | | | | |
| Gly | Ile | Thr | Val | Trp | Gly | Ser | Ser | Asp | Pro | Asp | Ser | Trp | Arg | Ser | Ser | |
| | | 290 | | | | 295 | | | | | 300 | | | | | |
| Ser | Ser | Pro | Leu | Leu | Phe | Asp | Ser | Asn | Tyr | Asn | Pro | Lys | Ala | Ala | Tyr | |
| 305 | | | | | 310 | | | | | 315 | | | | | 320 | |
| Thr | Ala | Ile | Ala | Asn | Ala | Leu | Trp | Ser | Ser | Leu | Ser | Leu | Val | Lys | Leu | |
| | | | | 325 | | | | | 330 | | | | | 335 | | |
| Ala | Ala | Ser | Arg | Ile | Gln | Leu | Glu | Cys | Arg | Arg | Asp | Arg | Arg | Met | Asn | |
| | | | 340 | | | | | 345 | | | | | 350 | | | |
| Thr | Arg | Gly | Leu | Arg | Val | Ala | Phe | Ser | Val | Phe | Ser | Pro | Glu | Val | Ile | |
| | | 355 | | | | | 360 | | | | | 365 | | | | |
| Ile | Met | Leu | Leu | Asn | Leu | Pro | Leu | Leu | Leu | Leu | Ile | Asn | Gly | Glu | His | |
| | 370 | | | | | 375 | | | | | 380 | | | | | |
| Arg | Phe | Ile | Tyr | Lys | Lys | Lys | Lys | Lys | Lys | Lys | Lys | Lys | | | | |
| 385 | | | | | 390 | | | | | 395 | | | | | | |

( 2 ) INFORMATION FOR SEQ ID NO:3:

( i ) SEQUENCE CHARACTERISTICS:
        ( A ) LENGTH: 1327 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(4..1221, 1225..1314, 1318..1326)

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| AAA | ATG | GTC | GGA | CTG | CTT | TCA | ATC | ACC | GCG | GCG | CTT | GCC | GCG | ACT | GTG | 48 |
| | Met | Val | Gly | Leu | Leu | Ser | Ile | Thr | Ala | Ala | Leu | Ala | Ala | Thr | Val | |
| | 1 | | | | 5 | | | | | 10 | | | | | 15 | |
| TTG | CCA | AAC | ATT | GTC | TCT | GCC | GTT | GGT | CTG | GAT | CAG | GCT | GCA | GTT | GCC | 96 |
| Leu | Pro | Asn | Ile | Val | Ser | Ala | Val | Gly | Leu | Asp | Gln | Ala | Ala | Val | Ala | |
| | | | | 20 | | | | | 25 | | | | | 30 | | |
| AAA | GGA | CTT | CAA | TAC | TTT | GGC | ACA | GCT | ACG | GAT | AAT | CCC | GAG | CTC | ACG | 144 |
| Lys | Gly | Leu | Gln | Tyr | Phe | Gly | Thr | Ala | Thr | Asp | Asn | Pro | Glu | Leu | Thr | |
| | | | 35 | | | | | 40 | | | | | 45 | | | |
| GAT | ATT | CCA | TAC | GTT | ACT | CAG | CTG | AAC | AAC | ACC | GCG | GAC | TTT | GGT | CAA | 192 |
| Asp | Ile | Pro | Tyr | Val | Thr | Gln | Leu | Asn | Asn | Thr | Ala | Asp | Phe | Gly | Gln | |
| | | 50 | | | | | 55 | | | | | 60 | | | | |
| ATT | ACC | CCT | GGA | AAC | TCG | ATG | AAG | TGG | GAT | GCC | ACA | GAA | CCA | TCT | CAG | 240 |
| Ile | Thr | Pro | Gly | Asn | Ser | Met | Lys | Trp | Asp | Ala | Thr | Glu | Pro | Ser | Gln | |
| | 65 | | | | | 70 | | | | | 75 | | | | | |
| GGC | ACC | TTC | ACG | TTC | ACG | AAA | GGC | GAT | GTC | ATT | GCA | GAT | CTG | GCT | GAG | 288 |
| Gly | Thr | Phe | Thr | Phe | Thr | Lys | Gly | Asp | Val | Ile | Ala | Asp | Leu | Ala | Glu | |
| 80 | | | | | 85 | | | | | 90 | | | | | 95 | |
| GGT | AAT | GGC | CAA | TAT | CTC | CGA | TGT | CAT | ACT | CTG | GTT | TGG | TAT | AAT | CAG | 336 |
| Gly | Asn | Gly | Gln | Tyr | Leu | Arg | Cys | His | Thr | Leu | Val | Trp | Tyr | Asn | Gln | |
| | | | | 100 | | | | | 105 | | | | | 110 | | |
| CTA | CCT | AGC | TGG | GTG | ACT | AGC | GGA | ACT | TGG | ACT | AAT | GCT | ACT | CTC | ACC | 384 |

```
Leu Pro Ser Trp Val Thr Ser Gly Thr Trp Thr Asn Ala Thr Leu Thr
        115                 120                 125

GCC GCA TTG AAG AAC CAC ATC ACG AAT GTG GTG TCG CAC TAC AAA GGG      432
Ala Ala Leu Lys Asn His Ile Thr Asn Val Val Ser His Tyr Lys Gly
        130                 135                 140

AAA TGT CTT CAT TGG GAC GTG GTC AAT GAG GCG TTG AAT GAC GAC GGA      480
Lys Cys Leu His Trp Asp Val Val Asn Glu Ala Leu Asn Asp Asp Gly
        145                 150                 155

ACC TAC CGC ACC AAC ATC TTC TAC ACC ACC ATC GGC GAA GCC TAC ATC      528
Thr Tyr Arg Thr Asn Ile Phe Tyr Thr Thr Ile Gly Glu Ala Tyr Ile
160                 165                 170                 175

CCC ATT GCC TTT GCC GCA GCG GCT GCA GCC GAC CCG GAC GCG AAG CTG      576
Pro Ile Ala Phe Ala Ala Ala Ala Ala Ala Asp Pro Asp Ala Lys Leu
                180                 185                 190

TTC TAC AAT GAC TAC AAC CTC GAA TAC GGC GGC GCC AAA GCC GCC AGC      624
Phe Tyr Asn Asp Tyr Asn Leu Glu Tyr Gly Gly Ala Lys Ala Ala Ser
            195                 200                 205

GCC CGC GCC ATT GTC CAG CTG GTC AAG AAT GCA GGT GCC AAG ATC GAC      672
Ala Arg Ala Ile Val Gln Leu Val Lys Asn Ala Gly Ala Lys Ile Asp
        210                 215                 220

GGG GTA GGG TTG CAG GCC CAT TTC AGC GTC GGC ACC GTG CCG AGT ACG      720
Gly Val Gly Leu Gln Ala His Phe Ser Val Gly Thr Val Pro Ser Thr
        225                 230                 235

AGC TCG CTC GTC TCG GTG CTG CAA TCT TTC ACT GCG CTC GGG GTC GAG      768
Ser Ser Leu Val Ser Val Leu Gln Ser Phe Thr Ala Leu Gly Val Glu
240                 245                 250                 255

GTC GCC TAC ACG GAG GCC GAC GTG CGC ATT CTC CTG CCC ACC ACC GCC      816
Val Ala Tyr Thr Glu Ala Asp Val Arg Ile Leu Leu Pro Thr Thr Ala
                260                 265                 270

ACT ACC CTG GCC CAA CAG TCG AGC GAT TTC CAG GCC CTG GTG CAA TCC      864
Thr Thr Leu Ala Gln Gln Ser Ser Asp Phe Gln Ala Leu Val Gln Ser
            275                 280                 285

TGT GTG CAG ACA ACG GGC TGC GTC GGC TTC ACT ATC TGG GAT TGG ACA      912
Cys Val Gln Thr Thr Gly Cys Val Gly Phe Thr Ile Trp Asp Trp Thr
        290                 295                 300

GAT AAG TAC AGC TGG GTT CCC AGC ACG TTC TCG GGC TAT GGG GCG GCG      960
Asp Lys Tyr Ser Trp Val Pro Ser Thr Phe Ser Gly Tyr Gly Ala Ala
        305                 310                 315

CTA CCC TGG GAT GAG AAC CTG GTT AAG AAG CCC GCG TAC AAT GGC TTG     1008
Leu Pro Trp Asp Glu Asn Leu Val Lys Lys Pro Ala Tyr Asn Gly Leu
320                 325                 330                 335

TTG GCC GGC ATG GGG GTT ACA GTT ACC ACT ACG ACT ACC ACC ACC ACT     1056
Leu Ala Gly Met Gly Val Thr Val Thr Thr Thr Thr Thr Thr Thr Thr
                340                 345                 350

GCT ACT GCC ACT GGT AAG ACT ACG ACT ACC ACA ACG GGT GCC ACG AGC     1104
Ala Thr Ala Thr Gly Lys Thr Thr Thr Thr Thr Thr Gly Ala Thr Ser
            355                 360                 365

ACG GGG ACT ACG GCT GCG CAT TGG GGG CAG TGT GGA GGG CTC AAC TGG     1152
Thr Gly Thr Thr Ala Ala His Trp Gly Gln Cys Gly Gly Leu Asn Trp
        370                 375                 380

AGT GGA CCG ACG GCG TGT GCC ACT GGG TAC ACC TGC ACT TAT GTC AAT     1200
Ser Gly Pro Thr Ala Cys Ala Thr Gly Tyr Thr Cys Thr Tyr Val Asn
        385                 390                 395

GAC TAT TAC TCG CAG TGT CTG TGA AGT ATA GCC CAA CCT AAA CCT GCC     1248
Asp Tyr Tyr Ser Gln Cys Leu     Ser Ile Ala Gln Pro Lys Pro Ala
400                 405                     410

GGC GTG CTT GCC ATT CAG TCA GTG AGA TTT ATA TAT CAC AAT ACT CAA     1296
Gly Val Leu Ala Ile Gln Ser Val Arg Phe Ile Tyr His Asn Thr Gln
415                 420                 425                 430

AAT TCA TTG CTC GAC CTC TGA AAA AAA AAA A                           1327
```

Asn Ser Leu Leu Asp Leu        Lys Lys Lys
                    435

(2) INFORMATION FOR SEQ ID NO:4:

(i) SEQUENCE CHARACTERISTICS:
        (A) LENGTH: 439 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Gly Leu Leu Ser Ile Thr Ala Ala Leu Ala Ala Thr Val Leu
 1               5                  10                  15

Pro Asn Ile Val Ser Ala Val Gly Leu Asp Gln Ala Ala Val Ala Lys
                20                  25                  30

Gly Leu Gln Tyr Phe Gly Thr Ala Thr Asp Asn Pro Glu Leu Thr Asp
            35                  40                  45

Ile Pro Tyr Val Thr Gln Leu Asn Asn Thr Ala Asp Phe Gly Gln Ile
        50                  55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
        115                 120                 125

Ala Leu Lys Asn His Ile Thr Asn Val Val Ser His Tyr Lys Gly Lys
    130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Ala Asp Pro Asp Ala Lys Leu Phe
            180                 185                 190

Tyr Asn Asp Tyr Asn Leu Glu Tyr Gly Gly Ala Lys Ala Ala Ser Ala
        195                 200                 205

Arg Ala Ile Val Gln Leu Val Lys Asn Ala Gly Ala Lys Ile Asp Gly
210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
        275                 280                 285

Val Gln Thr Thr Gly Cys Val Gly Phe Thr Ile Trp Asp Trp Thr Asp
290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
            340                 345                 350
```

```
Thr  Ala  Thr  Gly  Lys  Thr  Thr  Thr  Thr  Thr  Gly  Ala  Thr  Ser  Thr
          355                      360                     365

Gly  Thr  Thr  Ala  Ala  His  Trp  Gly  Gln  Cys  Gly  Gly  Leu  Asn  Trp  Ser
     370                      375                     380

Gly  Pro  Thr  Ala  Cys  Ala  Thr  Gly  Tyr  Thr  Cys  Thr  Tyr  Val  Asn  Asp
385                      390                     395                          400

Tyr  Tyr  Ser  Gln  Cys  Leu  Ser  Ile  Ala  Gln  Pro  Lys  Pro  Ala  Gly  Val
               405                      410                          415

Leu  Ala  Ile  Gln  Ser  Val  Arg  Phe  Ile  Tyr  His  Asn  Thr  Gln  Asn  Ser
               420                      425                     430

Leu  Leu  Asp  Leu  Lys  Lys  Lys
               435
```

(2) INFORMATION FOR SEQ ID NO:5:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(31..723, 727..849, 853..900, 904..927)

(xi) SEQUENCE DESCRIPTION: SEQ ID NO:5:

```
TCCCTTCTAC  TTAGTATTCA  CTGACTTACC  ATG  GCT  CGC  CTA  TCT  CAG  TTC  CTT    54
                                    Met  Ala  Arg  Leu  Ser  Gln  Phe  Leu
                                     1                    5

CTG  GCC  TGC  GCT  CTT  GCA  GTC  AAA  GCC  TTC  GCT  GCC  CCC  GCC  GCC  GAG   102
Leu  Ala  Cys  Ala  Leu  Ala  Val  Lys  Ala  Phe  Ala  Ala  Pro  Ala  Ala  Glu
          10                      15                     20

CCC  GTC  GAG  GAA  CGG  GGC  CCT  AAC  TTC  TTT  TCT  GCC  CTT  GCT  GGG  CGC   150
Pro  Val  Glu  Glu  Arg  Gly  Pro  Asn  Phe  Phe  Ser  Ala  Leu  Ala  Gly  Arg
25                       30                      35                          40

TCG  ACT  GGC  AGC  TCC  ACT  GGC  TAC  TCG  AAC  GGC  TAT  TAC  TAT  AGC  TTC   198
Ser  Thr  Gly  Ser  Ser  Thr  Gly  Tyr  Ser  Asn  Gly  Tyr  Tyr  Tyr  Ser  Phe
               45                      50                          55

TGG  ACC  GAT  GGC  GCA  AGC  GGC  GAT  GTT  GAA  TAC  AGC  AAC  GGC  GCC  GGG   246
Trp  Thr  Asp  Gly  Ala  Ser  Gly  Asp  Val  Glu  Tyr  Ser  Asn  Gly  Ala  Gly
               60                      65                          70

GGG  TCC  TAC  AGC  GTG  ACC  TGG  TCA  TCG  GCC  TCG  AAC  TTC  GTC  GGT  GGA   294
Gly  Ser  Tyr  Ser  Val  Thr  Trp  Ser  Ser  Ala  Ser  Asn  Phe  Val  Gly  Gly
               75                      80                          85

AAG  GGC  TGG  AAC  CCT  GGA  AGT  GCT  CAT  GAC  ATT  ACG  TAC  TCC  GGC  TCC   342
Lys  Gly  Trp  Asn  Pro  Gly  Ser  Ala  His  Asp  Ile  Thr  Tyr  Ser  Gly  Ser
          90                      95                     100

TGG  ACC  AGC  ACA  GGA  AAT  AGC  AAC  AGC  TAC  CTC  TCC  GTC  TAC  GGC  TGG   390
Trp  Thr  Ser  Thr  Gly  Asn  Ser  Asn  Ser  Tyr  Leu  Ser  Val  Tyr  Gly  Trp
105                      110                     115                        120

ACC  ACC  GGT  CCT  CTC  GTC  GAG  TAC  TAT  ATC  CTG  GAG  GAC  TAC  GGG  GAG   438
Thr  Thr  Gly  Pro  Leu  Val  Glu  Tyr  Tyr  Ile  Leu  Glu  Asp  Tyr  Gly  Glu
               125                     130                         135

TAC  AAC  CCC  GGC  TCA  GCT  GGC  ACT  TAC  AAA  GGC  TCG  GTC  TAC  TCC  GAC   486
Tyr  Asn  Pro  Gly  Ser  Ala  Gly  Thr  Tyr  Lys  Gly  Ser  Val  Tyr  Ser  Asp
               140                     145                         150

GGA  TCG  ACA  TAC  AAT  ATC  TAC  ACG  GCG  ACC  CGC  ACC  AAC  GCC  CCC  TCC   534
Gly  Ser  Thr  Tyr  Asn  Ile  Tyr  Thr  Ala  Thr  Arg  Thr  Asn  Ala  Pro  Ser
               155                     160                         165
```

```
ATC  CAG  GGC  ACG  GCC  ACT  TTC  ACG  CAG  TAC  TGG  TCC  ATT  CGC  CAG  ACA     582
Ile  Gln  Gly  Thr  Ala  Thr  Phe  Thr  Gln  Tyr  Trp  Ser  Ile  Arg  Gln  Thr
     170                      175                      180

AAG  CGC  GTC  GGC  GGT  ACC  GTG  ACG  ACT  GCC  AAC  CAT  TTC  AAT  GCC  TGG     630
Lys  Arg  Val  Gly  Gly  Thr  Val  Thr  Thr  Ala  Asn  His  Phe  Asn  Ala  Trp
185                           190                      195                 200

GCG  AAG  CTG  GGA  ATG  AAT  CTG  GGC  ACG  CAC  AAC  TAT  CAG  ATC  GTC  GCT     678
Ala  Lys  Leu  Gly  Met  Asn  Leu  Gly  Thr  His  Asn  Tyr  Gln  Ile  Val  Ala
                    205                      210                      215

ACT  GAA  GGC  TAC  TAC  TCG  TCT  GGG  TCT  GCG  TCC  ATT  ACG  GTT  GCC          723
Thr  Glu  Gly  Tyr  Tyr  Ser  Ser  Gly  Ser  Ala  Ser  Ile  Thr  Val  Ala
                    220                      225                 230

TGA  GAG  CGT  GCA  GAT  ATC  CTG  CTG  CGA  TAT  ATG  CTG  TAT  CTC  TGG  CAC     771

CGT  TTC  TGT  GAT  GGC  AAT  GAG  TGG  ATG  AGG  AAG  TTG  GCT  TGT  TCG  TAC     819

ATG  AGC  AGG  GTG  GTA  GTA  TCG  GAA  TTT  GGA  TGA  GCA  TTG  GAT  TTC  GAA     867

TTA  TTT  TTT  ATT  CAA  TCT  CAG  CCT  CCA  GTT  TCG  TAG  CAA  CAA  GTA  AAA     915

AAA  AAA  AAA  AAA                                                                 927
```

( 2 ) INFORMATION FOR SEQ ID NO:6:

( i ) SEQUENCE CHARACTERISTICS:
        ( A ) LENGTH: 231 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ala  Arg  Leu  Ser  Gln  Phe  Leu  Leu  Ala  Cys  Ala  Leu  Ala  Val  Lys
1                   5                        10                      15

Ala  Phe  Ala  Ala  Pro  Ala  Ala  Glu  Pro  Val  Glu  Glu  Arg  Gly  Pro  Asn
               20                      25                      30

Phe  Phe  Ser  Ala  Leu  Ala  Gly  Arg  Ser  Thr  Gly  Ser  Ser  Thr  Gly  Tyr
          35                       40                      45

Ser  Asn  Gly  Tyr  Tyr  Tyr  Ser  Phe  Trp  Thr  Asp  Gly  Ala  Ser  Gly  Asp
     50                       55                      60

Val  Glu  Tyr  Ser  Asn  Gly  Ala  Gly  Gly  Ser  Tyr  Ser  Val  Thr  Trp  Ser
65                       70                      75                           80

Ser  Ala  Ser  Asn  Phe  Val  Gly  Gly  Lys  Gly  Trp  Asn  Pro  Gly  Ser  Ala
               85                       90                           95

His  Asp  Ile  Thr  Tyr  Ser  Gly  Ser  Trp  Thr  Ser  Thr  Gly  Asn  Ser  Asn
               100                      105                     110

Ser  Tyr  Leu  Ser  Val  Tyr  Gly  Trp  Thr  Thr  Gly  Pro  Leu  Val  Glu  Tyr
          115                      120                     125

Tyr  Ile  Leu  Glu  Asp  Tyr  Gly  Glu  Tyr  Asn  Pro  Gly  Ser  Ala  Gly  Thr
     130                      135                     140

Tyr  Lys  Gly  Ser  Val  Tyr  Ser  Asp  Gly  Ser  Thr  Tyr  Asn  Ile  Tyr  Thr
145                      150                     155                          160

Ala  Thr  Arg  Thr  Asn  Ala  Pro  Ser  Ile  Gln  Gly  Thr  Ala  Thr  Phe  Thr
               165                      170                     175

Gln  Tyr  Trp  Ser  Ile  Arg  Gln  Thr  Lys  Arg  Val  Gly  Gly  Thr  Val  Thr
               180                      185                     190

Thr  Ala  Asn  His  Phe  Asn  Ala  Trp  Ala  Lys  Leu  Gly  Met  Asn  Leu  Gly
               195                      200                     205

Thr  His  Asn  Tyr  Gln  Ile  Val  Ala  Thr  Glu  Gly  Tyr  Tyr  Ser  Ser  Gly
     210                      215                     220
```

```
Ser  Ala  Ser  Ile  Thr  Val  Ala
225                 230
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CATCAACATT CATTCATTCA     20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TTTAATTCAT TCCTCAAGCT     20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CAAGAGCAGT CATCCTTCT     20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TTCCAACATG GTTCAAATCA     20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

AAGCAGCTGC TCTGGCTGTC     20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

CTTTTCGCCA GCAATGTGCT     20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CTCCAACCCC ATCGAGCCCC G     21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CCAGGCCTCG GTGAGCATCG A     21

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TGCCAAATTA CAAGGCGCAC G     21

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CAAGAAGTAC CTGGGCACCA T     21

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (i i) MOLECULE TYPE: cDNA (x i) SEQUENCE DESCRIPTION: SEQ ID NO:17:

GAACCCCCAC AATCACGCAA 20

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:18:

AAATGGTCGG ACTGCTTTCA 20

(2) INFORMATION FOR SEQ ID NO:19:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:19:

ATCACCGCGG CGCTTGCCG 19

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:20:

CTGTGTTGCC AAACATTGTC 20

(2) INFORMATION FOR SEQ ID NO:21:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:21:

TCTGCCGTTG GTCTGGATCA 20

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:22:

GGCTGCAGTT GCCAAAGGAC 20

( 2 ) INFORMATION FOR SEQ ID NO:23:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:23:

TTCAATACTT TGGCACAGCT 20

( 2 ) INFORMATION FOR SEQ ID NO:24:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:24:

ACGGATAATC CCGAGCTCAC 20

( 2 ) INFORMATION FOR SEQ ID NO:25:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:25:

GGATATTCCA TACGTTACTC A 21

( 2 ) INFORMATION FOR SEQ ID NO:26:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:26:

GCTGAACAAC ACCGCGGACT 20

( 2 ) INFORMATION FOR SEQ ID NO:27:

( i ) SEQUENCE CHARACTERISTICS:
           ( A ) LENGTH: 23 base pairs
           ( B ) TYPE: nucleic acid
           ( C ) STRANDEDNESS: single
           ( D ) TOPOLOGY: linear ( i i ) MOLECULE TYPE: cDNA ( x i ) SEQUENCE DESCRIPTION: SEQ ID NO:27:

TTGGTCAAAT TACCCCTGGA AAC 23

( 2 ) INFORMATION FOR SEQ ID NO:28:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:28:

TCGATGAAGT GGGATGCCAC      20

( 2 ) INFORMATION FOR SEQ ID NO:29:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:29:

AGAACCATCT CAGGGCACCT TC      22

( 2 ) INFORMATION FOR SEQ ID NO:30:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:30:

ACGTTCACGA AAGGC      15

( 2 ) INFORMATION FOR SEQ ID NO:31:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:31:

CTTCTACTTA GTATTCA      17

( 2 ) INFORMATION FOR SEQ ID NO:32:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:32:

CTGACTTACC ATGGCTCGCC      20

( 2 ) INFORMATION FOR SEQ ID NO:33:

( i ) SEQUENCE CHARACTERISTICS:
  ( A ) LENGTH: 20 base pairs
  ( B ) TYPE: nucleic acid
  ( C ) STRANDEDNESS: single (D) TOPOLOGY: linear (i i) MOLECULE TYPE: cDNA (x i) SEQUENCE DESCRIPTION: SEQ ID NO:33:

TATCTCAGTT CCTTCTGGCC 20

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:34:

TGCGCTCTTG CAGTCAAAG 19

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:35:

CCTTCGCTGC CCCCGCCGCC 20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:36:

GAGCCCGTCG AGGAACGGGG 20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:37:

CCCTAACTTC TTTTCTGCCC 20

(2) INFORMATION FOR SEQ ID NO:38:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:38:

```
TTGCTGGGCG CTCGACTGG                                                                19
```

( 2 ) INFORMATION FOR SEQ ID NO:39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
CAGCTCCACT GGCTACTCGA A                                                             21
```

( 2 ) INFORMATION FOR SEQ ID NO:40:

( i ) SEQUENCE CHARACTERISTICS:
        ( A ) LENGTH: 204 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

```
CATCAACATT CATTCATTCA TTTAATTCAT TCCTCAAGCT CAAGAGCAGT CATCCCTTCT                   60

TTCCAACATG GTTCAAATCA AAGCAGCTGC TCTGGCTGTC CTTTTCGCCA GCAATGTGCT                   120

CTCCAACCCC ATCGAGCCCC GCCAGGCCTC GGTGAGCATC GATGCCAAAT TCAAGGCGCA                   180

CGGCAAGAAG TACCTGGGCA CCAT                                                          204
```

( 2 ) INFORMATION FOR SEQ ID NO:41:

( i ) SEQUENCE CHARACTERISTICS:
        ( A ) LENGTH: 265 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:41:

```
AAAATGGTCG GACTGCTTTC AATCACCGCG GCGCTTGCCG CGACTGTGTT GCCAAACATT                   60

GTCTCTGCCG TTGGTCTGGA TCAGGCTGCA GTTGCCAAAG GACTTCAATA CTTTGGCACA                   120

GCTACGGATA ATCCCGAGCT CACGGATATT CCATACGTTA CTCAGCTGAA CAACACCGCG                   180

GACTTTGGTC AAATTACCCC TGGAAACTCG ATGAAGTGGG ATGCCACAGA ACCATCTCAG                   240

GGCACCTTCA CGTTCACGAA AGGCG                                                         265
```

( 2 ) INFORMATION FOR SEQ ID NO:42:

( i ) SEQUENCE CHARACTERISTICS:
        ( A ) LENGTH: 179 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

```
TCCCTTCTAC TTAGTATTCA CTGACTTACC ATGGCTCGCC TATCTCAGTT CCTTCTGGCC                   60
```

```
TGCGCTCTTG  CAGTCAAAGC  CTTCGCTGCC  CCCGCCGCCG  AGCCCGTCGA  GGAACGGGGC      120

CCTAACTTCT  TTTCTGCCCT  TGCTGGGCGC  TCGACTGGCA  GCTCCACTGG  CTACTCGAA       179
```

ENZYME WITH XYLANASE ACTIVITY

This application is a divisional application of co-pending application Ser. No. 08/507,431, filed Feb. 15, 1996, now U.S. Pat. No. 5,693,518, which is a 35 U.S.C. 371 national application of PCT/DK94/00088 filed Mar. 2, 1994 and claims priority of Danish application Serial Nos. 0268/93 and 1151/93 filed Mar. 10, 1993 Oct. 14, 1993, respectively, the contents of which are fully incorporated herein by reference in their entirety.

FIELD OF INVENTION

The present invention relates to an enzyme with xylanase activity, a method of producing the enzyme, an enzyme preparation containing the enzyme, and use of the enzyme for various industrial purposes.

BACKGROUND OF THE INVENTION

Xylan, a major component of plant hemicellulose, is a polymer of D-xylose linked by beta-1,4-xylosidic bonds. Xylan can be degraded to xylose and xylo-oligomers by acid or enzymatic hydrolysis. Enzymatic hydrolysis of xylan produces free sugars without the by-products formed with acid (e.g. furans).

Enzymes which are capable of degrading xylan and other plant cell wall polysaccharides are important for the food industry, primarily for baking and in fruit and vegetable processing such as fruit juice production or wine making, where their ability to catalyse the degradation of the backbone or side chains of the plant cell wall polysaccharide is utilised (Visser et al., Xylans and Xylanases, 1991).

Other applications for xylanases are enzymatic breakdown of agricultural wastes for production of alcohol fuels, enzymatic treatment of animal feeds for hydrolysis of pentosans, manufacturing of dissolving pulps yielding cellulose, and bio-bleaching of wood pulp [Detroym R. W. In: Organic Chemicals from Biomass, (CRC Press, Boca Raton, Fla., 1981) 19–41.; Paice, M. G., and L. Jurasek., J. Wood Chem. Technol. 4: 187–198.; Pommier, J. C., J. L. Fuentes, G. Goma., Tappi Journal (1989): 187–191.; Senior, D. J., et al., Biotechnol. Letters 10 (1988):907–912].

WO 92/17573 discloses a substantially pure xylanase derived from the fungal species *H. insolens* and recombinant DNA encoding said xylanase. The xylanase is stated to be useful as a baking agent, a feed additive, and in the preparation of paper and pulp.

WO 92/01793 discloses a xylanase derived from the fungal species *Aspergillus tubigensis*. It is mentioned, but not shown that related xylanases may be derived from other filamentous fungi, examples of which are Aspergillus, Disporotrichum, Penicillium, Neurospora, Fusarium and Trichoderma. The xylanases are stated to be useful in the preparation of bread or animal feed, in breewing and in reducing viscosity or improving filterability of cereal starch.

Shei et al., 1985, and Fournier et al., 1985 describe purification and characterization of endoxylanases isolated from A. niger.

WO 91/19782 and EP 463 706 discloses xylanase derived from *Aspergillus niger* origin and the recombinant production thereof. The xylanase is stated to be useful for baking, brewing, in the paper making industry, and in the treatment of agricultural waste, etc.

SUMMARY OF THE INVENTION

It is an object of the present invention to prepare single-component xylanases.

Accordingly, the present invention relates to an enzyme exhibiting xylanase activity, which enzyme is immunologically reactive with an antibody raised against a purified xylanase derived from *Aspergillus aculeatus*, CBS 101.43.

In the present context, the term "derived from" is intended not only to indicate a xylanase produced by strain CBS 101.43, but also a xylanase encoded by a DNA sequence isolated from strain CBS 101.43 and produced in a host organism transformed with said DNA sequence.

In another aspect, the invention relates to an enzyme exhibiting xylanase activity, which enzyme is encoded by a DNA sequence comprising at least one of the following partial sequences (a) CATCAACATT CATTCATTCA (SEQ ID No. 7)
(b) TTTAATTCAT TCCTCAAGCT (SEQ ID No. 8)
(c) CAAGAGCAGT CATCCCTTCT (SEQ ID No. 9)
(d) TTCCAACATG GTTCAAATCA (SEQ ID No. 10)
(e) AAGCAGCTGC TCTGGCTGTC (SEQ ID No. 11)
(f) CTTTTCGCCA GCAATGTGCT (SEQ ID No. 12)
(g) CTCCAACCCC ATCGAGCCCG (SEQ ID No. 13)
(h) CCAGGCCTCG GTGAGCATCGA (SEQ ID No. 14)
(i) TGCCAAATTA CAAGGCGCACG (SEQ ID No. 15)
(j) CAAGAAGTAC CTGGGCACCAT (SEQ ID No. 16)
(k) GAACCCCCAC AATCACGCAA (SEQ ID No. 17)
(l) AAATGGTCGG ACTGCTTTCA (SEQ ID No. 18)
(m) ATCACCGCGG CGCTTGCCG (SEQ ID No. 19)
(n) CTGTGTTGCC AAACATTGTC (SEQ ID No. 20)
(o) TCTGCCGTTG GTCTGGATCA (SEQ ID No. 21)
(p) GGCTGCAGTT GCCAAAGGAC (SEQ ID No. 22)
(q) TTCAATACTT TGGCACAGCT (SEQ ID No. 23)
(r) ACGGATAATC CCGAGCTCAC (SEQ ID No. 24)
(s) GGATATTCCAT ACGTTACTCA (SEQ ID No. 25)
(t) GCTGAACAAC ACCGCGGACT (SEQ ID No. 26)
(u) TTGGTCAAAT TACCCCTGGAAAC (SEQ ID No. 27)
(v) TCGATGAAGT GGGATGCCAC (SEQ ID No. 28)
(w) AGAACCATCT CAGGGCACCTTC (SEQ ID No. 29)
(x) ACGTTCACGA AAGGC (SEQ ID No. 30)
(y) CTTCTACTTA GTATTCA (SEQ ID No. 31)
(z) CTGACTTACC ATGGCTCGCC (SEQ ID No. 32)
(A) TATCTCAGTT CCTTCTGGCC (SEQ ID No. 33)
(B) TGCGCTCTTG CAGTCAAAG (SEQ ID No. 34)
(C) CCTTCGCTGC CCCCGCCGCC (SEQ ID No. 35)
(D) GAGCCCGTCG AGGAACGGGG (SEQ ID No. 36)
(E) CCCTAACTTC TTTTCTGCCC (SEQ ID No. 37)
(F) TTGCTGGGCG CTCGACTGG (SEQ ID No. 38)
(G) CAGCTCCACT GGCTACTCGAA (SEQ ID No. 39)

In further aspects the invention relates to an enzyme exhibiting xylanase activity, which enzyme is encoded by a DNA sequence comprised in or comprising a DNA sequence shown in any of SEQ ID Nos. 1, 3 or 5, respectively, or sequence homologous thereto encoding a polypeptide with xylanase activity.

The enzyme encoded by the DNA sequence shown in SEQ ID No. 1 is termed xylanase I (or xyl I) in the following disclosure, the enzyme encoded by the DNA sequence SEQ ID No. 3 is termed xylanase II (or xyl II) in the following disclosure, and the enzyme encoded by the DNA sequence SEQ ID No. 5 is termed xylanase III (or xyl III) in the following disclosure.

In a further aspect, the invention relates to an enzyme exhibiting xylanase activity, which enzyme is encoded by a DNA sequence comprising the following partial sequence
CATCAACATT CATTCATTCA TTTAATTCAT TCCT-
CAAGCT CAAGAGCAGT
CATCCCTTCT TTCCAACATG GTTCAAATCA AAG-
CAGCTGC TCTGGCTGTC
CTTTTCGCCA GCAATGTGCT CTCCAACCCC ATC-
GAGCCCC GCCAGGCCTC GGTGAGCATC GATGCCAAAT TCAAGGCGCA CGGCAAGAAG TACCTGGGCA CCAT
(SEQ ID No. 40)

or a sequence homologous thereto encoding a polypeptide with xylanase activity. A particular example of such enzyme is xylanase I as defined above.

In a still further aspect, the invention relates to an enzyme exhibiting xylanase activity, which enzyme is encoded by a DNA sequence comprising the following partial sequence
AAAATGGTCG GACTGCTTTC AATCACCGCG GCGCTTGCCG CGACTGTGTT
GCCAAACATT GTCTCTGCCG TTGGTCTGGA TCAGGCTGCA GTTGCCAAAG
GACTTCAATA CTTTGGCACA GCTACGGATA ATCCCGAGCT CACGGATATT
CCATACGTTA CTCAGCTGAA CAACACCGCG GACTTTGGTC AAATTACCCC
TGGAAACTCG ATGAAGTGGG ATGCCACAGA ACCATCTCAG GGCACCTTCA
CGTTCACGAAAGGCG (SEQ ID NO. 41)

or a sequence homologous thereto encoding a polypeptide with xylanase activity. A particular example of such enzyme is xylanase II as defined above.

In a still further aspect, the invention relates to an enzyme exhibiting xylanase activity, which enzyme is encoded by a DNA sequence comprising the following partial sequence
TCCCTTCTAC TTAGTATTCA CTGACTTACC ATGGCTCGCC TATCTCAGTT
CCTTCTGGCC TGCGCTCTTG CAGTCAAAGC CTTCGCTGCC CCCGCCGCCG
AGCCCGTCGA GGAACGGGG CCTAACTTCT TTTCTGCCCT TGCTGGGCGC
TCGACTGGCA GCTCCACTGG CTACTCGAA
(SEQ ID No. 42)

or a sequence homologous thereto encoding a polypeptide with xylanase activity. A particular example of such enzyme is xylanase III as defined above.

In the present context, the term "homologue" is intended to indicate a polypeptide encoded by DNA which hybridizes to the same probe as the DNA coding for the xylanase enzyme under certain specified conditions (such as presoaking in 5× SSC and prehybridizing for 1 h at −40° C. in a solution of 5× SSC, 5× Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at −40° C. followed by washing three times in 2× SSC, 0.2% SDS at 40° C. for 30 minutes). More specifically, the term is intended to refer to a DNA sequence which is at least 70% homologous to any of the sequences shown above encoding a xylanase of the invention, such as at least 75%, at least 80%, at least 85%, at least 90% or even at least 95% homologous to any of the sequences shown above. The term is intended to include modifications of any of the DNA sequences shown above, such as nucleotide substitutions which do not give rise to another amino acid sequence of the xylanase, but which correspond to the codon usage of the host organism into which the DNA construct is introduced or nucleotide substitutions which do give rise to a different amino acid sequence and therefore, possibly, a different protein structure which might give rise to a xylanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In a still further aspect, the present invention relates to an enzyme preparation useful for the degradation of plant cell wall components, said preparation being enriched in an enzyme exhibiting xylanase activity as described above.

In final aspects the invention relates to the use of an enzyme or enzyme preparation of the invention for various industrial applications.

DETAILED DESCRIPTION OF THE INVENTION

Figure 1:
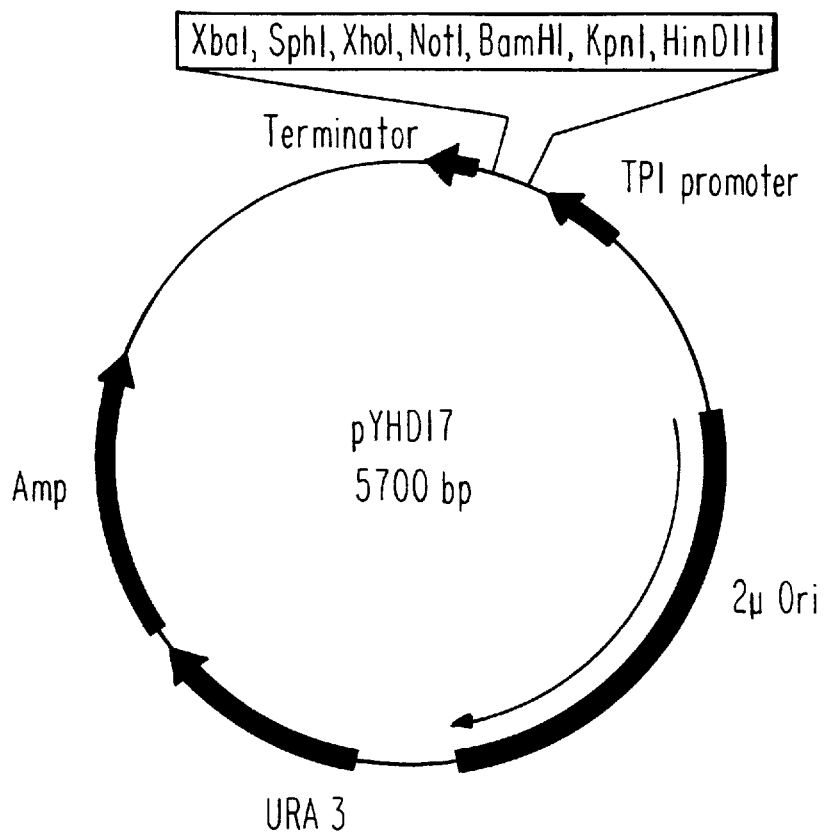

In a preferred embodiment the enzyme of the invention comprises or is comprised in the amino acid sequence apparent from SEQ ID Nos. 2, 4 and 6, respectively, or an analogous sequence thereof. The amino acid sequences shown in these SEQ ID's have been deduced from the DNA sequences shown in SEQ ID Nos. 1, 3 and 5, respectively, encoding xylanase I, II and III as defined above.

In the present context, the term "analogous sequence" is intended to indicate an amino acid sequence differing from that of SEQ ID No. 2, 4 and 6, respectively, by one or more amino acid residues. The analogous sequence may be one resulting from modification of an amino acid sequence shown in these SEQ ID's, e.g. involving substitution of one or more amino acid residues at one or more different sites in the amino acid sequence, deletion of one or more amino acid residues at either or both ends of the enzyme or at one or more sites in the amino acid sequence, or insertion of one or more amino acid residues at one or more sites in the amino acid sequence. The modification of the amino acid sequence may suitably be performed by modifying the DNA sequence encoding the enzyme, e.g. by site-directed or by random mutagenesis or a combination of these techniques in accordance with well-known procedures. Alternatively, the analogous sequence may be one of an enzyme derived from another origin than the xylanase corresponding to SEQ ID Nos. 2, 4 and 6, respectively. The analogous sequence will normally exhibit a degree of homology (in terms of identity) of at least 70%, such as at least 75%, 80%, 85%, 90% or even 95% with the amino acid sequence shown in SEQ ID Nos. 2, 4 and 6, respectively.

It has surprisingly been found that xylanase II of the present invention in addition to xylanase activity exhibits α-arabinopyranosidase activity.

The enzyme of the invention may be isolated by a general method involving cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any xylanase activity of the enzyme produced by such clones.

A more detailed description of this screening method is given in Example 1 below. expressing the appropriate enzyme activity (i.e. xylanase activity as defined by the ability of the enzyme to hydrolyse glycosidic bonds in xylan). The appropriate DNA sequence may then be isolated from the clone by standard procedures, e.g. as described in Example 1. It is expected that a DNA sequence coding for a homologous enzyme may be derived by similarly screening a cDNA library of another microorganism, in particular a fungus, such as a strain of another *Aspergillus sp.*, in particular a strain of *A. aculeatus* or *A. niger*, a strain of a *Trichoderma sp.*, in particular a strain of *T. harzianum*, or *T. reesie*, a strain of a *Fusarium sp.*, in particular a strain of *F. oxysporum*, or a strain of a *Humicola sp.* or a strain of *Scytallidium sp.*

Alternatively, the DNA coding for an xylanase of the invention may, in accordance with well-known procedures, conveniently be isolated from DNA from any of the above mentioned organisms by use of synthetic oligonucleotide probes prepared on the basis of a DNA or amino acid sequence disclosed herein. For instance, a suitable oligonucleotide probe may be prepared on the basis of any of the partial nucleotide sequences (a)–(G) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the xylanase should be operably connected to a suitable promoter and terminator replicated together with the chromosome(s) into which it has been integrated.

In the vector, the DNA sequence encoding the xylanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the xylanase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed xylanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified xylanase may be employed for immunization of animals for the production of antibodies. More specifically, antiserum against the xylanase of the invention may be raised by immunizing rabbits (or other rodents) according to the procedure described by N. Axelsen et al. in: *A Manual of quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4$)$_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

In a still further aspect, the present invention relates to an enzyme preparation useful for the degradation of plant cell wall components, said preparation being enriched in an enzyme exhibiting xylanase activity as described above. In this manner a boosting of the cell wall degrading ability of the enzyme preparation can be obtained.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast or Celluzyme (all available from Novo Nordisk A/S). In the present context, the term "enriched" is intended to indicate that the xylanase activity of the enzyme preparation has been increased, e.g. with an enrichment factor of 1.1, conveniently due to addition of an enzyme of the invention prepared by the method described above.

Alternatively, the enzyme preparation enriched in an enzyme exhibiting xylanase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to a xylanase of the invention, contain one or more other plant cell wall degrading enzymes, for instance those with cellulytic, xylanolytic or pectinolytic activities such as α-arabinosidase, α-glucoronisidase, β-xylosidase, xylan acetyl esterase, arabinanase, rhamnogalacturonase, pectin acetylesterase, galactanase, polygalacturonase, pectin lyase, pectate lyase, glucanase or pectin methylesterase. The additional enzyme(s) may be producible by means of a microorganism belonging to the genus Aspergillus, preferably *Aspergillus niger, Aspergillus aculeatus, Aspergillus awamori* or *Aspergillus oryzae*, or Trichoderma.

The enzyme preparation according to the invention is preferably used as an agent for degradation or modification of plant cell walls or any xylan-containing material originating from plant cells walls due to the high plant cell wall degrading activity of the xylanase of the invention.

Examples are given below of preferred uses of the enzyme preparation of the invention. The dosage of the enzyme preparation of the invention and other conditions under which the preparation is used may be determined on the basis of methods known in the art.

The xylanases of the invention hydrolysis β-1,4 linkages in xylans. Xylans are polysaccharides having a backbone composed of β-1,4 linked xylose. The backbone may have different sidebranches, like arabinose, acetyl, glucuronic acid, 4-methylglucuronic acid sidebranches. The composition and number of sidebranches vary according to the source of the xylan. Arabinose sidebranches dominate in xylans from cereal endosperm, whereas xylans from hard wood contain relatively more acetyl and glucuronic acid substituents (Michael P. Coughlan and Geoffrey P. Hazlewood. Biotechnol.Appl. Biochem. 17 : 259–289 (1993). Xylan originating from red algae contains a mixture of β-1,4 and β-1,3 linked xylose in the backbone, this type of xylan is degradable by xylanases to varying extent due to the 1,4-links in the backbone.

The degradation of xylan by xylanases is facilitated by full or partial removal of the sidebranches. Acetyl groups can be removed by alkali, or by xylan acetyl-esterases, arabinose sidegroups can be removed by a mild acid treatment or by alpha-arabinosidases and the glucuronic acid sidebranches can be removed by alpha-glucuronisidases. The oligomers which are released by the xylanases, or by a combination of xylanases and sidebranch-hydrolysing enzymes as mentioned above can be further degraded to free xylose by beta-xylosidases.

Xylanases of the present invention can be used without other xylanolytic enzymes or with limited activity of other xylanolytic enzymes to degrade xylans for production of oligosaccharides. The oligosaccharides may be used as bulking agents, like arabinoxylan oligosaccharides released from cereal cell wall material, or of more or less purified arabinoxylans from cereals.

Xylanases of the present invention can be used in combination of other xylanolytic enzymes to degrade xylans to xylose and other monosaccharides. The released xylose may be converted to other compounds like furanone flavours.

Xylanases of the present invention may be used alone or together with other enzymes like glucanases to improve the extraction of oil from oil-rich plant material, like corn-oil from corn-embryos.

Xylanases of the present invention may be used in baking so as to improve the development, elasticity and/or stability of dough and/or the volume, crumb structure and/or antistaling properties of the baked product. Although the xylanases may be used for the preparation of dough or baked products prepared from any type of flour or meal (e.g. based on rye, barley, oat, or maize) xylanases of the invention have been found to be particularly useful in the preparation of dough or baked products made from wheat or comprising substantial amounts of wheat. The baked products produced with an xylanase of the invention includes bread, rolls, baquettes and the like. For baking purposes the xylanase of the invention may be used as the only or major enzymatic activity, or may be used in combination with other enzymes such as a lipase, an amylase, an oxidase (e.g. glucose oxidase, peroxidase), a laccase and/or a protease.

Xylanases of the present invention may be used for modification of animal feed and may exert their effect either in vitro (by modifying components of the feed) or in vivo. The xylanases are particularly suited for addition to animal feed compositions containing high amounts of arabinoxylans and glucuronoxylans, e.g. feed containing cereals such as barley, wheat, rye or oats or maize. When added to feed the xylanase significantly improves the in vivo break-down of plant cell wall material partly due to a reduction of the intestinal viscosity (Bedford et al., 1993), whereby a better utilization of the plant nutrients by the animal is achieved. Thereby, the growth rate and/or feed conversion ratio (i.e. the weight of ingested feed relative to weight gain) of the animal is improved. The use of a xylanase of the invention in the preparation of feed is illustrated in Example 8.

Xylanases of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process (Eriksson, K. E. L., Wood Science and Technology 24 (1990): 79–101; Paice, et al., Biotechnol. and Bioeng. 32 (1988): 235–239 and Pommier et al., Tappi Journal (1989): 187–191). Furthermore, the xylanases may be used for treatment of lignocellulosic pulp so as to improve the bleachability thereof. Thereby the amount of chlorine need to obtain a satisfactory bleaching of the pulp may be reduced. The treament of lignocellulosic pulp may, e.g., be performed as described in WO 93/08275, WO 91/02839 and WO 92/03608.

Xylanases of the present invention may be used in beer brewing, in particular to improve the filterability of wort e.g. containing barley and/or sorghum malt. The xylanases may be used in the same manner as pentosanases conventionallly used for brewing, e.g. as described by Viëtor et al., 1993 and EP 227 159. Furthermore, the xylanases may be used for treatment of brewers spent grain, i.e. residuals from beer wort production containing barley or malted barley or other cereals, so as to improve the utilization of the residuals for, e.g., animal feed.

Xylanases of the present invention may be used for separation of components of plant cell materials, in particular of cereal components such as wheat components. Of particular interest is the separation of wheat into gluten and starch, i.e. components of considerable commercial interest. The separation process may be performed by use of methods known in the art, conveniently a so-called batter process (or wet milling process) performed as a hydroclone or a decanter process. In the batter process, the starting material is a dilute pumpable dispersion of the plant material such as wheat to be subjected to separation. In a wheat separation process the dispersion is made normally from wheat flour and water.

Xylanases of the invention may also be used in the preparation of fruit or vegetable juice in order to increase yield, and in the enzymatic hydrolysis of various plant cell wall-derived materials or waste materials, e.g. from paper production, or agricultural residues such as wheat-straw, corn cobs, whole corn plants, nut shells, grass, vegetable hulls, bean hulls, spent grains, sugar beet pulp, and the like.

The plant material may be degraded in order to improve different kinds of processing, facilitate purification or extraction of other component than the xylans like purification of beta-glucan or beta-glucan oligomers from cereals, improve the feed value, decrease the water binding capacity, improve the degradability in waste water plants, improve the conversion of e.g. grass and corn to ensilage, etc.

Finally, xylanases of the invention may be used in modifying the viscosity of plant cell wall derived material. For instance, the xylanases may be used to reduce the viscosity of feed containing xylan, to promote processing of viscous xylan containing material as in wheat separation, and to reduce viscosity in the brewing process.

The invention is further described in the accompanying drawing in which

Figure 2:
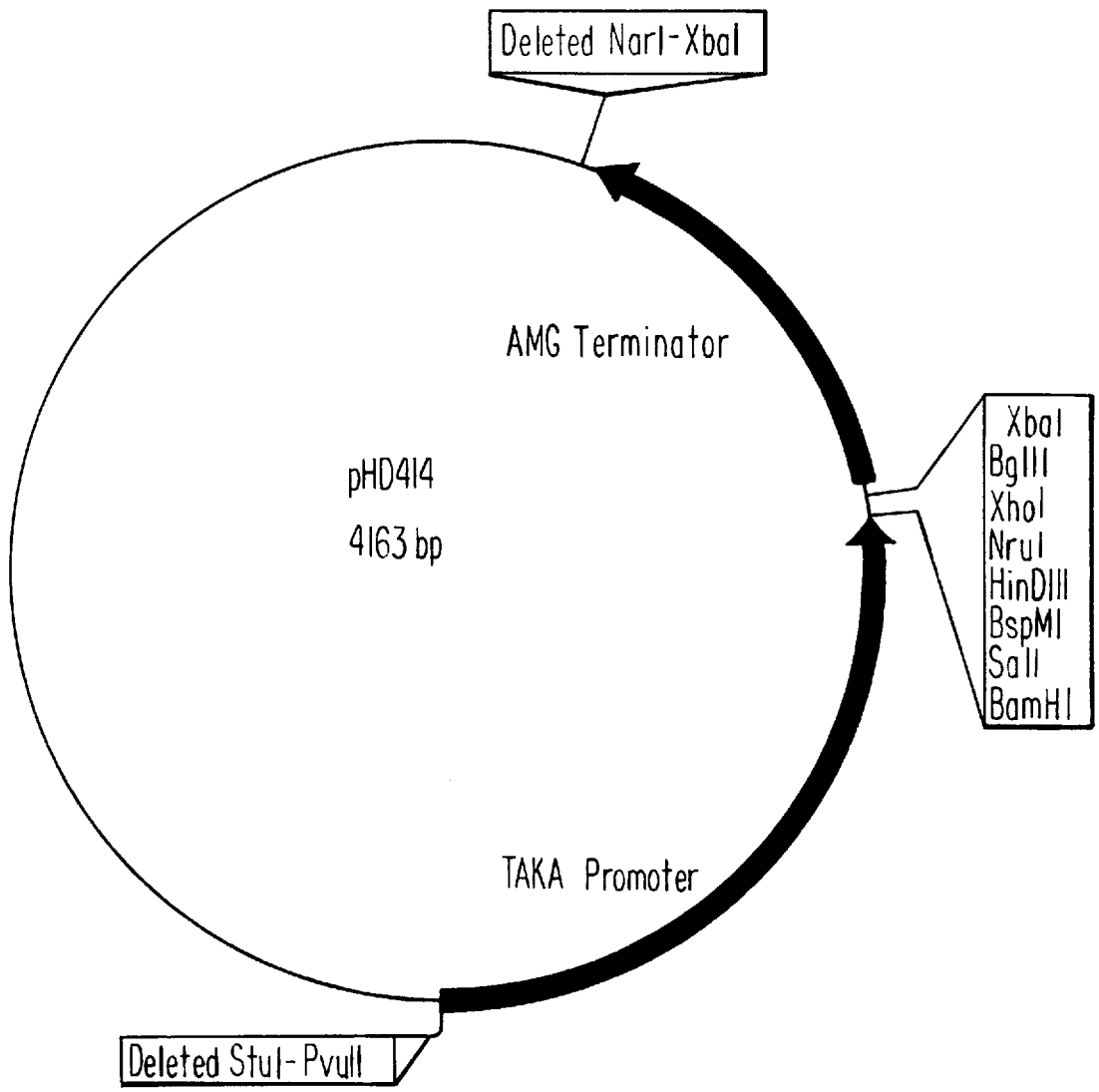
Figure 3:
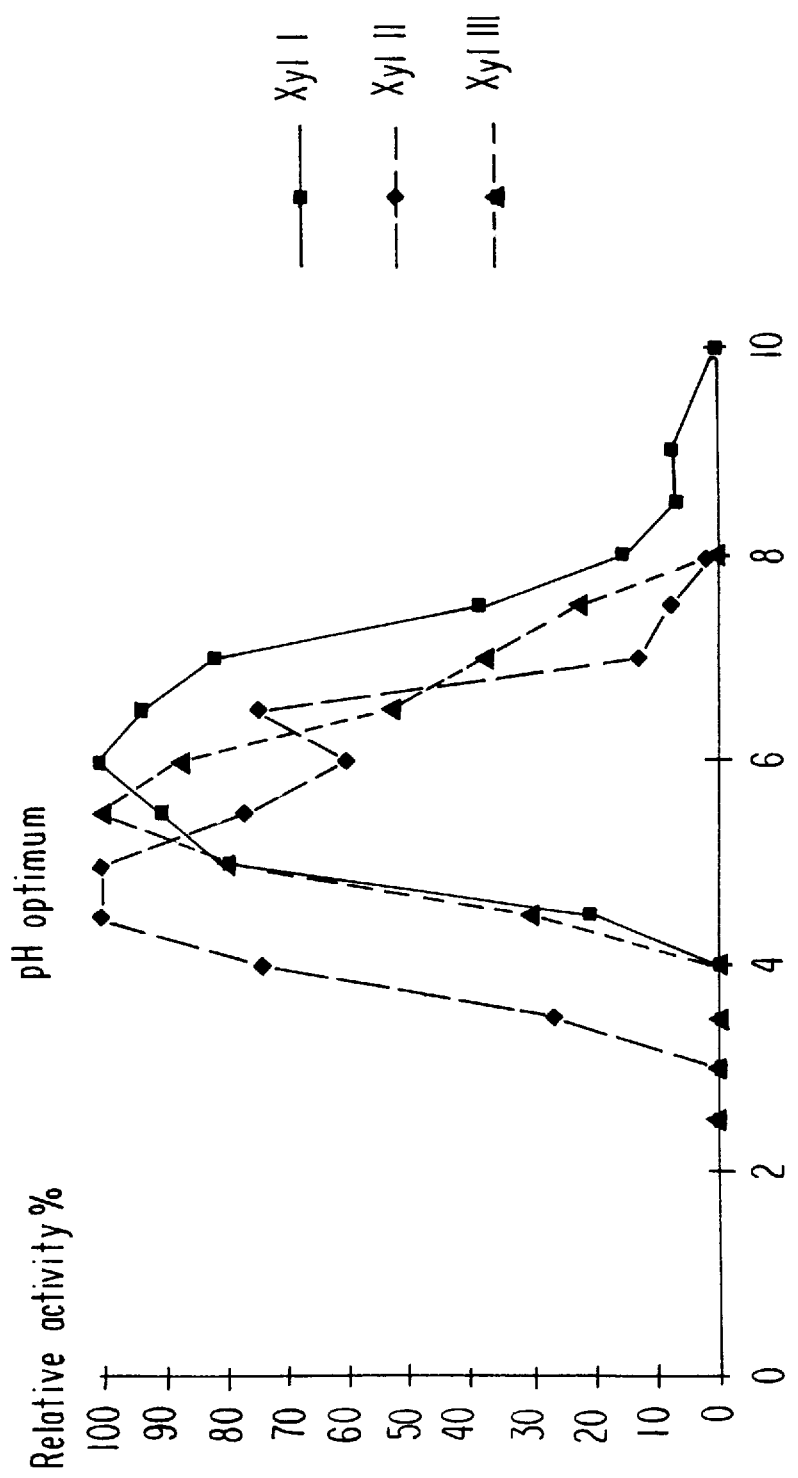
Figure 4:
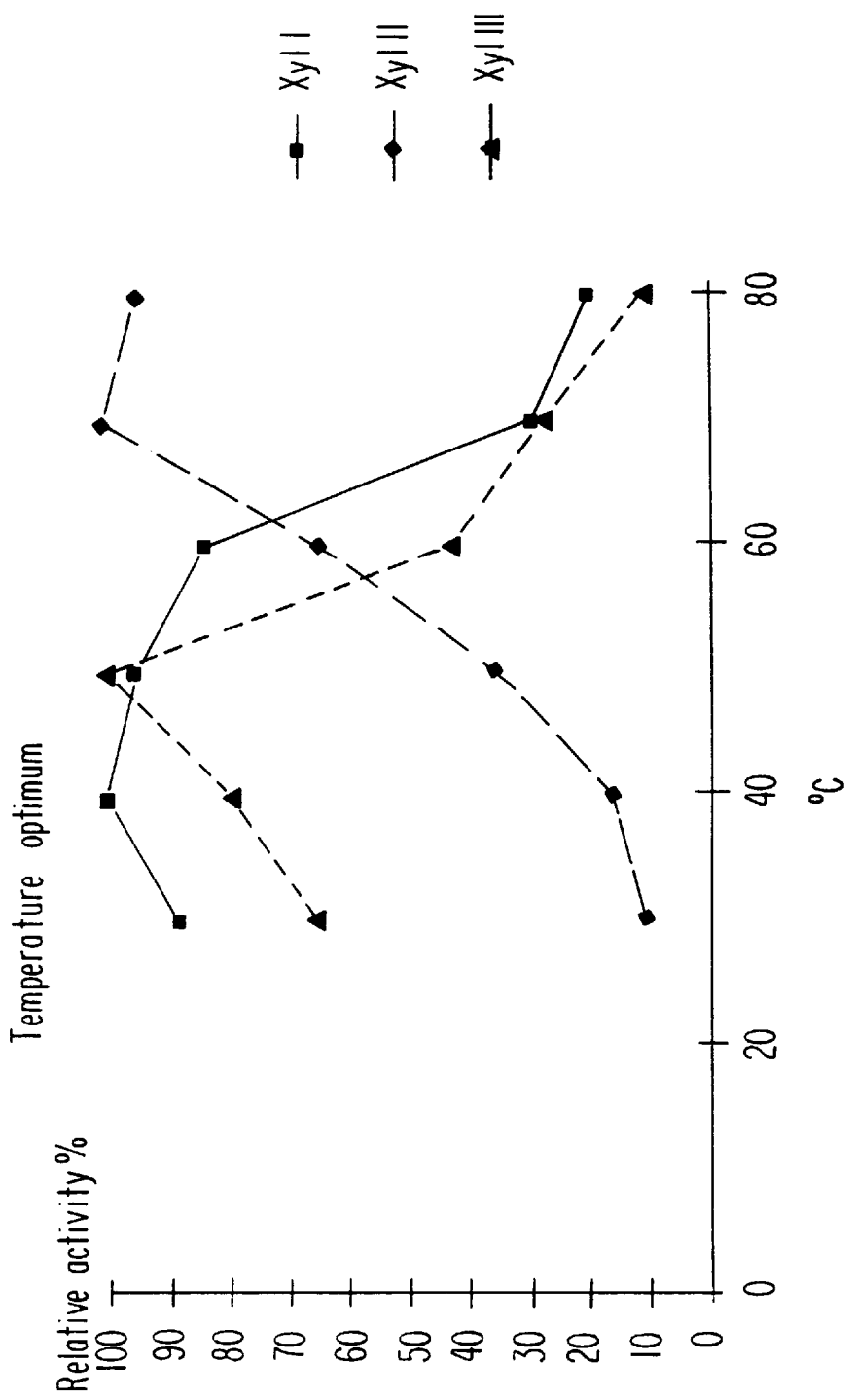
Figure 5:
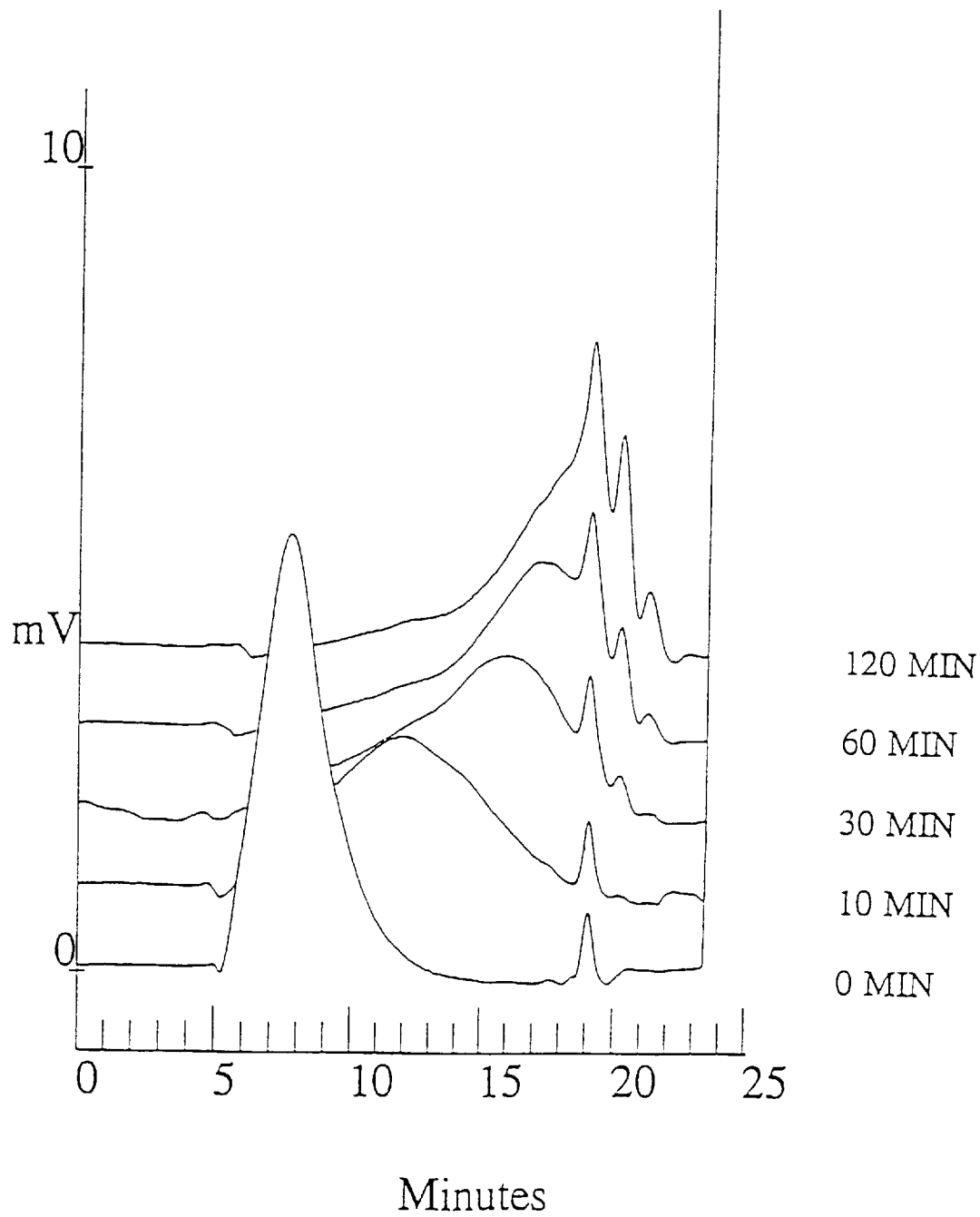
Figure 6:
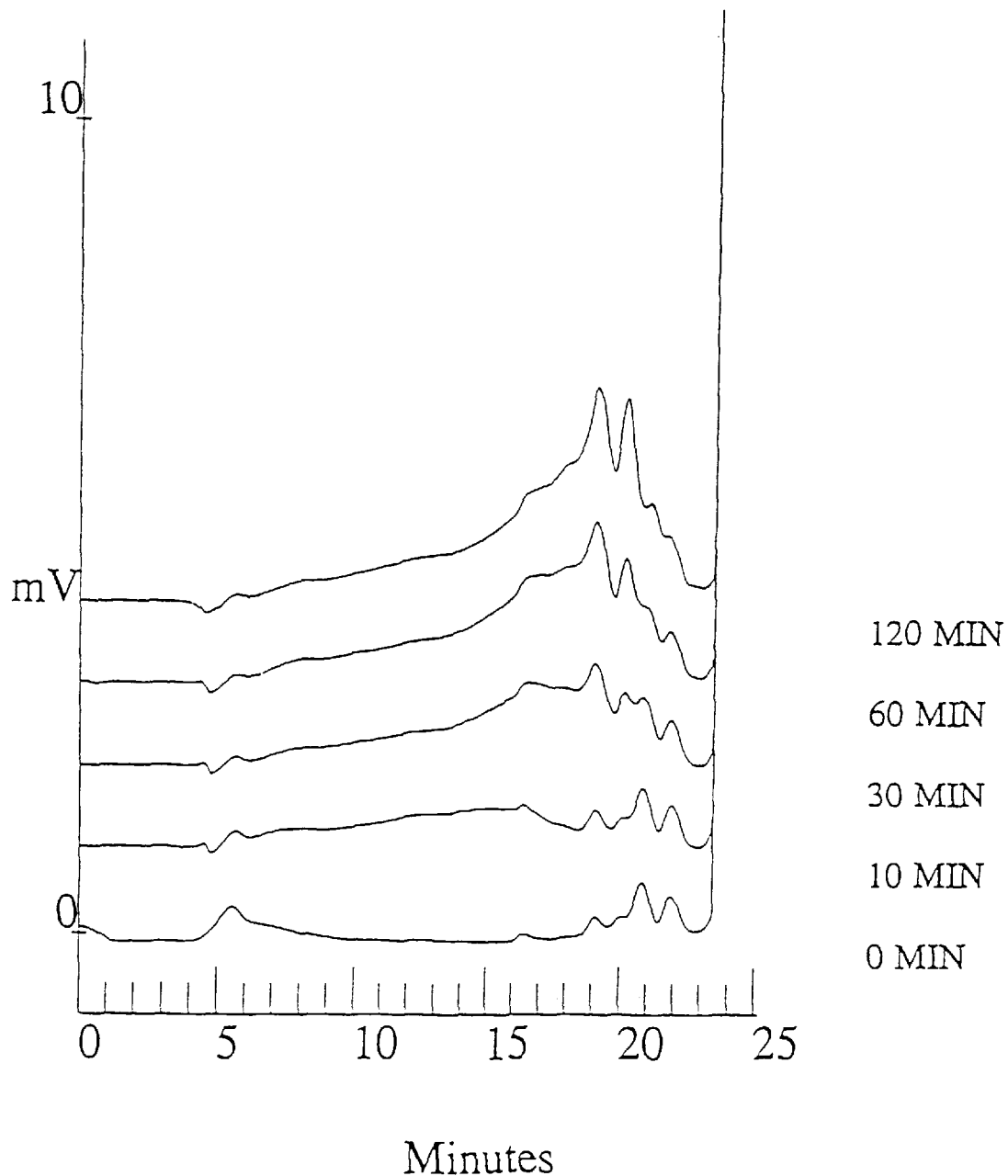
Figure 7:
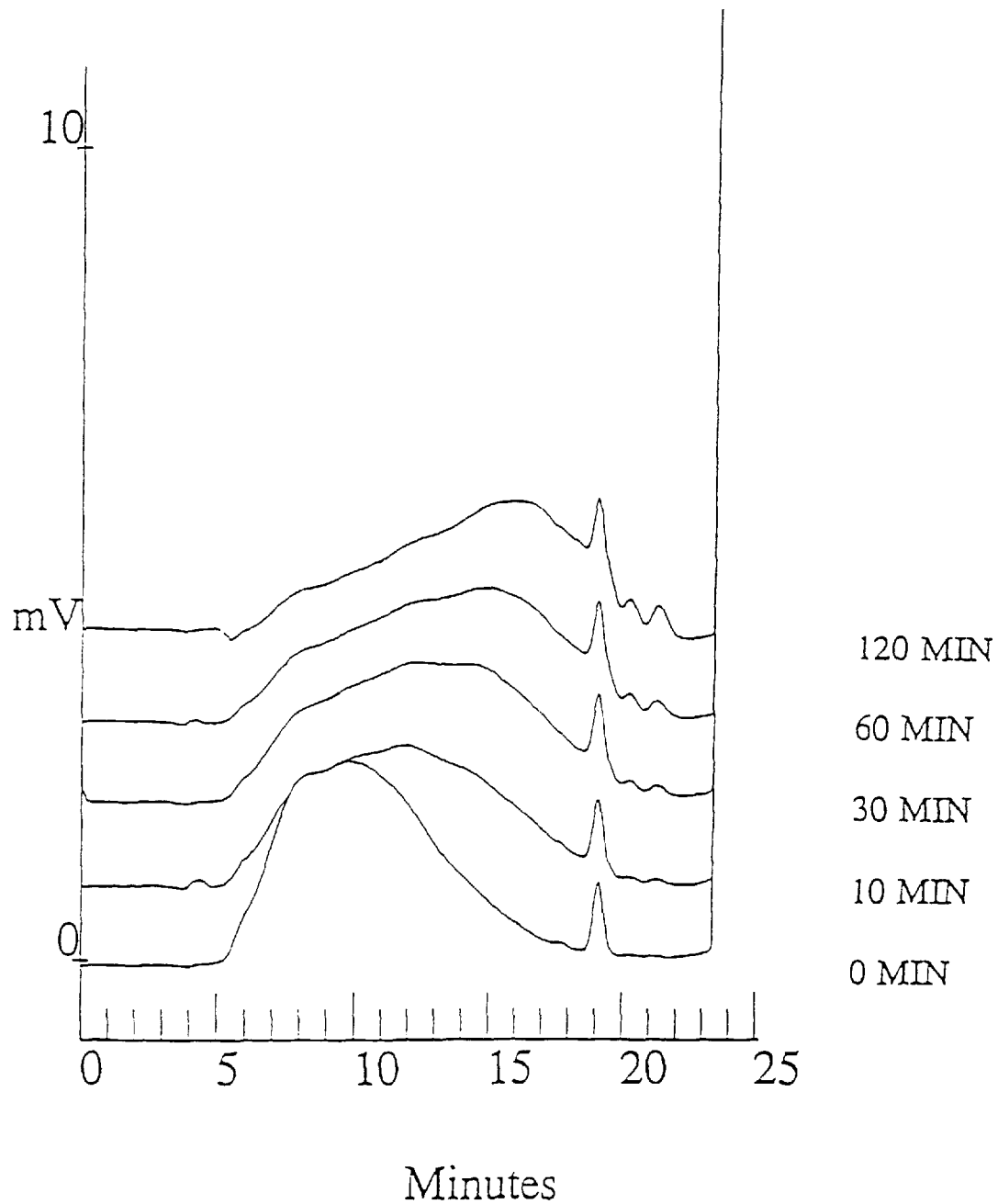
Figure 8:
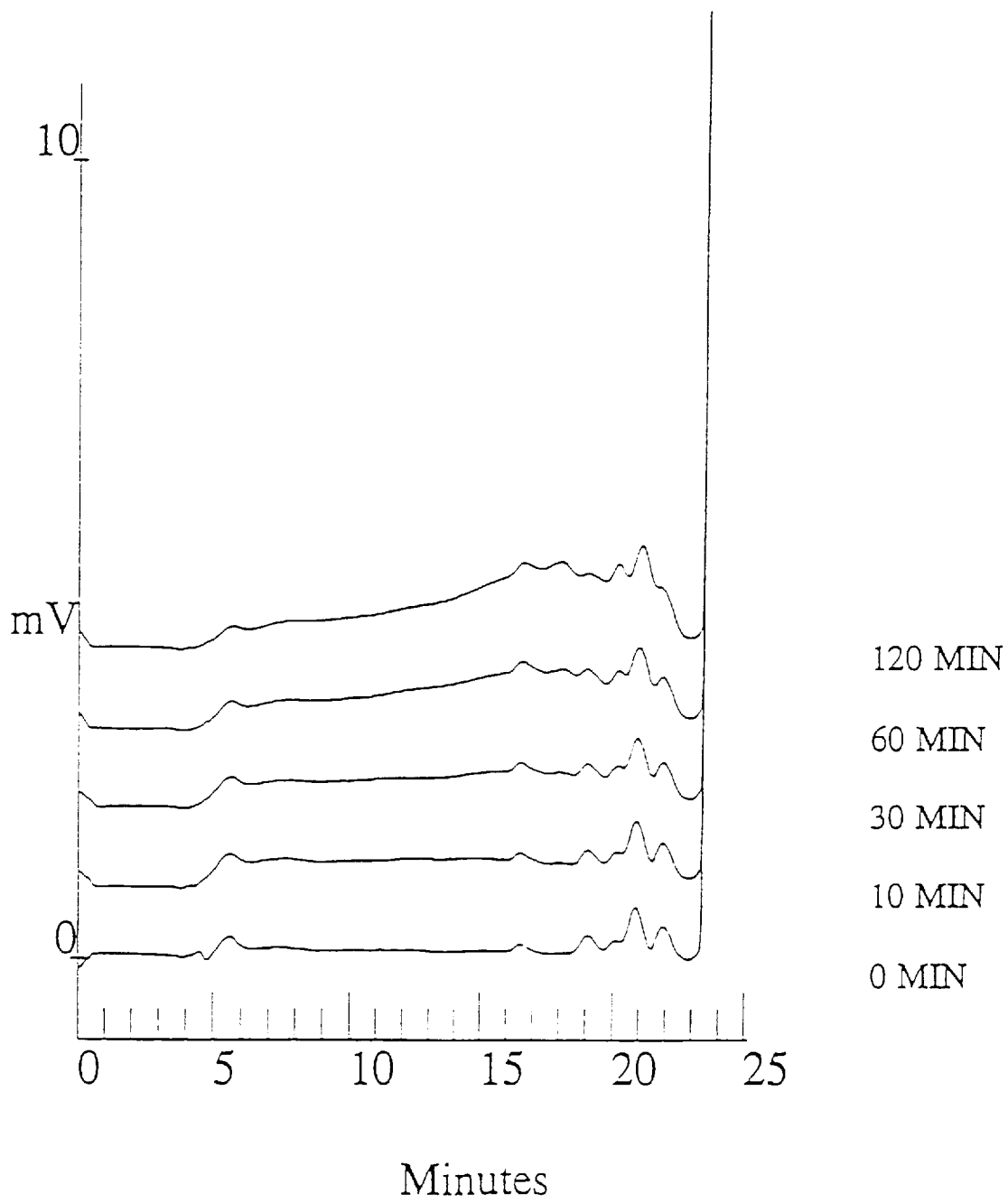
Figure 9:
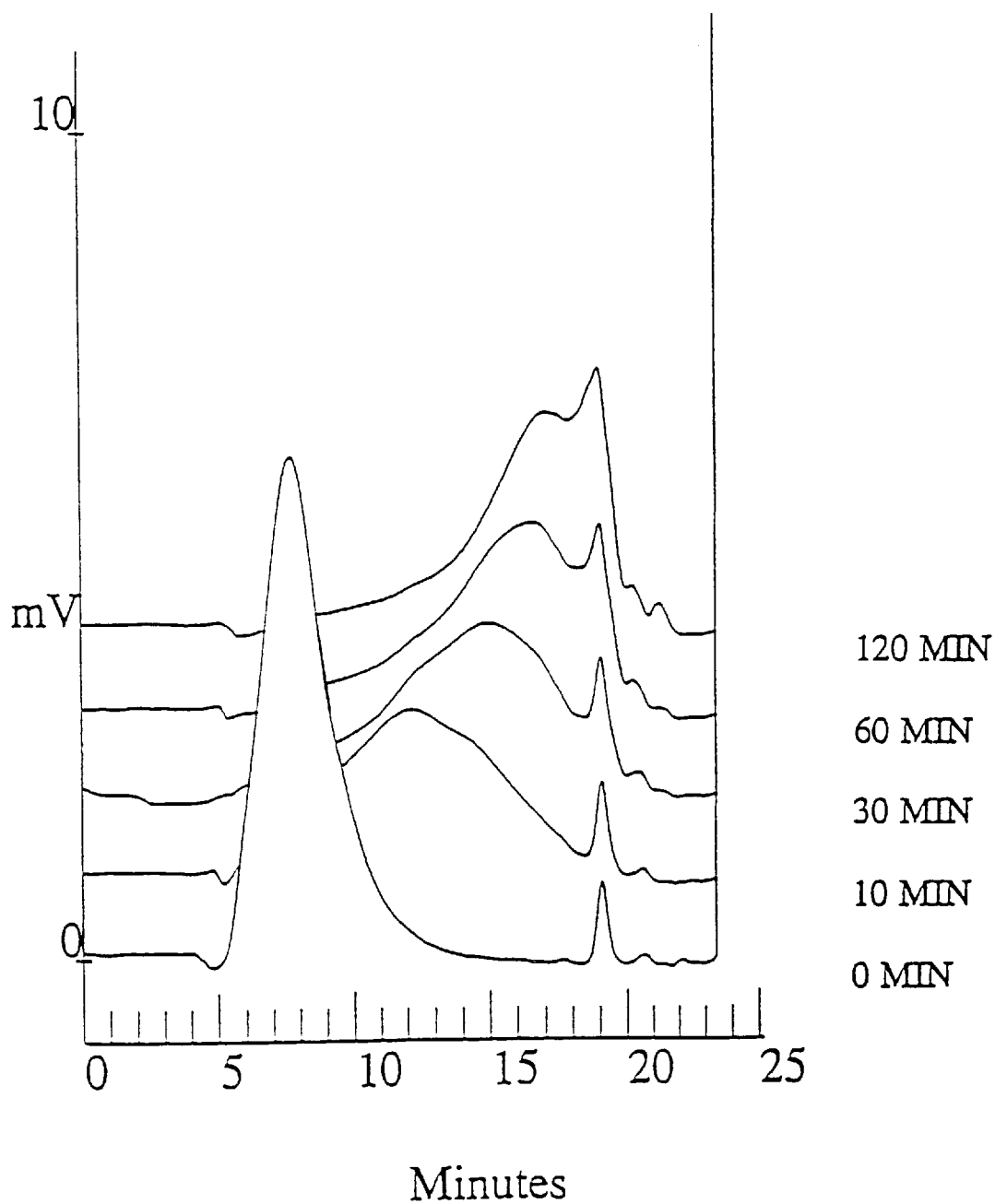
Figure 10:
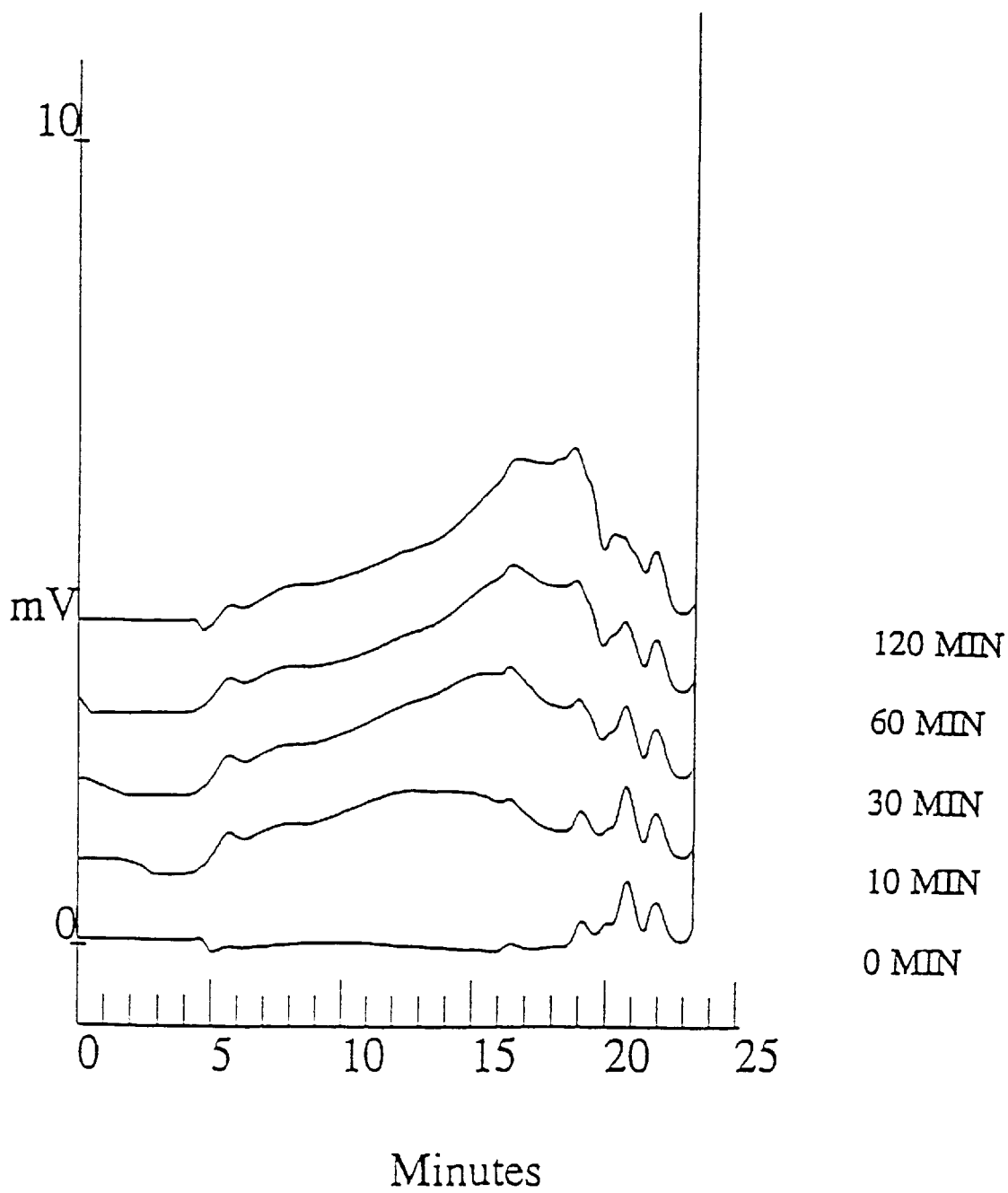

FIG. 1 is a restriction map of plasmid pYHD17,

FIG. 2 a restriction map of plasmid pHD 414,

FIG. 3 the pH optimums for Xyl I, Xyl II and xyl III,

FIG. 4 the temperature optimum for Xyl I, Xyl II and Xyl III,

FIG. 5 the gelfiltration chromatogram for degradation of 1% wheat-arabinoxylan degraded Xyl I, FIG. 6 the gelfiltration chromatogram for degradation of 5% WIP by Xyl I, FIG. 7 the gelfiltration chromatogram for degradation of 1% wheat-arabinoxylan by Xyl II, FIG. 8 the gelfiltration chromatogram for degradation of 5% WIP by Xyl II, FIG. 9 the gelfiltration chromatogram for degradation of 1% wheat-arabinoxylan by Xyl III, FIG. 10 the gelfiltration chromatogram for degradation of 5% WIP by Xyl III.

The invention is described in further detail in the following examples which are not in any way intended to limit the scope of the invention as claimed.

EXAMPLES

Materials and Methods

Donor organism: mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prc1::HIS3; prb1:: LEU2; cir+).

Construction of an expression plasmid: The commercially available plasmid pYES II (Invitrogen) was cut with SpeI, filled in with Klenow DNA polymerase +DNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Ball exonuclease treatment followed by addition of a SphI linker. Finally, an EcoRI linker was added at position −10. After these modifications, the promoter is included in a SphI-EcoRI fragment. Its effeciency compared to the original promoter appears to be unaffected by the modifications. The resulting plasmid pYHD17 is shown in FIG. 1.

Preparation of RNase-free glassware, tips and solutions: All glassware used in RNA isolations was baked at+220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA: The total RNA was prepared by extraction with guanidinium thiocyanate followed by ultracentrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GUSCN, 0.5% Na-laurylsarcosine, 25 mM Na-citrate, pH 7.0, 0.1M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25 000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 μl TE, pH 7.6 (if difficult, heat occasionally for 5 min at 65° C.), phenol extracted and precipitated with ethanol for 12 h at −200° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)$^+$ RNA: The poly(A)$^+$ RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1M NaCl, 1 mM EDTA, 0.1% SDS), followed by elution of the poly(A)$^+$ RNA with 3 vols of elution buffer (10 mM Tris-Cl, pH 7.6, 1 mM EDTA, 0.05% SDS) preheated to +65° C., by collecting 500 μl fractions. The $OD_{260}$ was read for each collected fraction, and the mRNA containing fractions were pooled and ethanol precipitated at −20° C. for 12 h. The poly(A)$^+$ RNA was collected by centrifugation, resuspended in DEPC-DIW and stored in 5–10 μg aliquots at −80° C.

Northern blot analysis: The poly(A)$^+$ RNAs (5 μg/sample) from various mycelia were electrophoresed in 1.2 agarose-2.2M formaldehyde gels (Sambrook et al., 1989) and blotted to nylon membranes (Hybond-N, Amersham) with 10× SSC (Sambrook et al., 1989) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from A. aculeatus (described in Danish Patent Application DK 1545/92), 2) a 1.3 kb Not I-Spe I fragment encoding endoglucanase I from *A. aculeatus* (described in DK 0419/92) and 3) a 1.2 kb Eag I fragment for galactanase I from *A. aculeatus* (described in WO 92/13945). Northern hybridizations were carried out in 5× SSC (Sambrook et al., 1989), 5× Denhardt's solution (Sambrook et al., 1989), 0.5% SDS (w/v) and 100 μg/ml denatured salmon sperm DNA with a probe concentration of ca. 2 ng/ml for 16 h at 65° C. followed by washes in 5× SSC at 65° C. (2×15 min), 2× SSC, 0.5% SDS (1×30 min), 0.2× SSC, 0.5% SDS (1×30 min), and 5× SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA Synthesis:

First strand synthesis: Double-stranded cDNA was synthesized from 5 µg of *A. aculeatus* poly(A)$^+$ RNA by the RNase H method (Gubler & Hoffman 1983, Sambrook et al., 1989) using the hair-pin modification. The poly(A)$^+$ RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H$^-$ reverse transcriptase (Bethesda Research Laboratories). First-strand cDNA was synthesized by incubating the reaction mixture at 45° C. for 1 h.

Second strand synthesis: After synthesis 30 µl of 10 mM Tris-Cl, pH 7.5, 1 mM EDTA was added, and the mRNA:cDNA hybrids were ethanol precipitated for 12 h at −20° C. by addition of 40 µg glycogen carrier (Boehringer Mannheim) 0.2 vols 10M NH$_4$Ac and 2.5 vols 96% EtOH. The hybrids were recovered by centrifugation, washed in 70% EtOH, air dried and resuspended in 250 µl of second strand buffer (20 mM Tris-Cl, pH 7.4, 90 mM KCl, 4.6 mM MgCl2, 10 mM (NH$_4$)$_2$SO$_4$, 16 µM BNAD$^+$) containing 100 µM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) cDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection: After the fill-in reaction the cDNA was ligated to non-palindromic BstX I adaptors (1 µg/µl, Invitrogen) in 30 µl of ligation buffer (50 mM Tris-Cl, pH 7.8, 10 mM MgCl2, 10 mM DTT, 1MM ATP, 25 µg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of CDNA libraries: The adapted, ds cDNA was recovered by centrifugation, washed in 70% EtOH and resuspended in 25 ml DIW. Prior to large-scale library ligation, four test ligations were carried out in 10 µl of ligation buffer (same as above) each containing 1 µl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector (either PYES 2.0 vector Invitrogen or yHD13). The ligation reactions were performed by incubation at +16° C. for 12 h, heated at 70° C. for 5 min, and 1 µl of each ligation electroporated (200 Ω, 2.5 kV, 25 µF) to 40 µl competent *E. coli* 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at 37° C. for 1 h, 50 µl plated on LB+ampicillin plates (100 µg/ml) and grown at 37° C. for 12 h.

Using the optimal conditions a large-scale ligation was set up in 40 µl of ligation buffer containing 9 units of T4 ligase, and the reaction was incubated at 16° C. for 12 h. The ligation reaction was stopped by heating at 70° C. for 5 min, ethanol precipitated at −20° C. for 12 h, recovered by centrifugation and resuspended in 10 µl DIW. One µl aliquots were transformed into electrocompetent *E. coli* 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 µl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One µl aliquots of purified plasmid DNA (100 ng/µl) from individual pools were electroporated (200 Ω, 1.5 kV, 25 µF) into 40 µl competent S. cerevisiae JG 169 cells (OD600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80 µl aliquots were plated on SC+glucose−uracil to give 250–400 c.f.u./plate and incubated at 30° C. for 3–5 days.

Construction of an Aspergillus expression vector: the vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. PHD413 was cut with StuI (positioned in the 5' end of the promoter) and PvuII (in the pUC vetor), fractionated on gel and religated. The plasmid pHD 414 is shown in FIG. 2.

Media

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth: 7.5 g/l yeast nit rogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrog en base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

AZCL xylan: birchwood or oat spelt xylan available from Megazyme, Australia.

4-methyl-umbelliferyl-α-arabinopyranoside: avaiable from Sigma.

Transformation of Aspergillus oryzae or Aspergillus niger (general procedure) 100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC. 100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem.Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Fed Batch Fermentation

Fed batch fermentation was performed in a medium comprising maltodextrin as a carbon source, urea as a nitrogen source and yeast extract. The fed batch fermentation was performed by innoculating a shake flask culture of A. oryzae host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered by centrifugation, ultrafiltration, clear filtration and germ filtration. For application experiments, amylase activity was reduced to an insignificant level by purification methods known in the art. For characterization, the enzymes were completely purified by anionexchange chromatographic methods known in the art.

Characterization of an Enzyme of the Invention

SDS-PAGE Electrophoresis: SDS-PAGE electrophoresis was performed in a Mini-Leak 4 electrophoresis unit (Kem-En-Tec, Copenhagen) as a modified version of the Laemli procedure (Laemmli, 1970; Christgau, 1991). Briefly, the separation gel was cast with 12% acrylamide; 0.2% BIS acrylamide; 0.1% SDS; 0.375M Tris pH 8.8; 0.04% APS (ammonium-persulphate) & 0.04% TEMED. After 6–15 hours of polymerization the stacking gel was cast with 4.5% w/w Acrylamide; 0.075% BIS-acrylamide; 0.1% SDS; 66.5 mM Tris pH 6.8; 0.4% w/w APS (ammonium persulphate) & 0.4% TEMED. The electrode chambers are filled with running buffer: 25 mM Tris-base; 0.192M glycine & 0.05% SDS, whereafter the samples containing sample buffer are loaded, and the gel is run at 2–4 mA/gel for over-night running and 10–30 mA/gel for fast running. The gel is subsequently removed and stained by either commassie or silver staining.

Isoelectric focusing: Isoelectric focusing is carried out on Ampholine PAG plates pH 3.5–9.5 (Pharmacia, Upsala) on a Multiphor electrophoresis unit according to the manufactures instructions. After electrophoresis the gel is either commassie stained or silver stained.

Commassie and silver staining: The gel is carefully removed from the glass plates and incubated on a slowly rotating shaking table in approximately 100 ml of the following solutions:

Commassie staining
1) 30 min in 40% v/v ethanol; 5% v/v acetic acid
2) 30 min in 40% v/v ethanol; 5% v/v acetic acid+0.1% Commassie R250
3) Destaining in 30 min in 40% v/v ethanol; 5% v/v acetic acid until background is sufficiently reduced.
4) Finally the gel is incubated in preserving solution : 5% v/v acetic acid; 10% v/v ethanol; 5% v/v glycerol and air dried between two sheets of cellophane membrane.

Silver staining
1) 30 min in 40% v/v ethanol; 5% v/v acetic acid 2) 20 min in 10% v/v ethanol; 5% v/v acetic acid
3) 20 min in 0.0057% w/v APS (0.25 mM)
4) 60 min in 0.1% w/v AgNO$_3$
5) For development, the gel is dipped in developer: 0.015% formaldehyde; 2% w/v Na$_2$CO$_3$ for 30–60 sec. Then the gel is incubated in a second round of developer until satisfactory staining of the proteins has been achieved (5–15 min.). Finally the gel is incubated in preserving solution: 5% v/v acetic acid; 10% v/v ethanol; 5% v/v glycerol and air dried between two sheets of cellophane membrane.

The activities of the enzymes are measured either by the release of reducing sugars from birch xylan (available from Roth, Karlsruhe, Germany) or by the release of blue colour from AZCL-birch xylan from MegaZyme.

0.5 ml 0.4% AZCL-substrate suspension is mixed with 0.5 ml 0.1M citrate/phosphate buffer of optimal pH and 10 µl of a suitably diluted enzyme solution is added. Incubations are carried out in Eppendorf Thermomixers for 15 minutes at 30° C. (if not otherwise specified) before heat-inactivation for 20 minutes at 95° C. Enzyme incubations are carried out in triplicate. A blank is produced in which enzyme is added but inactivated immediately. After centrifugation the absorbance of the supernatant is measured in microtiter plates at 620 nm and the blank is subtracted.

0.5% solutions of birch xylan (Roth) are made in 0.1M citrate/phosphate of the optimal pH, (if not otherwise specified) 10 µl enzyme suitably diluted solutions are added to 1 ml of substrate, incubations are carried out at 30° C. for 15 minutes before heat-inactivation as above. Reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks are subtracted. Xylose is used as a s tandard.

pH and temperature optimums are measured on the above mentioned substrates. 0.1M citrate/phosphate buffers of var ying pH are used f or d etermination of pH optimum. 0.1M citrate/phosphate buffers at optimal pH is used for reaction at different temperatures for 15 min. in order to determine the temperature optimum.

Km and specific activity are measured by carrying out incubations at substrate concentrations (S) ranging from 0.025 to 1.5% (birch xylan), measure the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

For gelfiltration chromatography 1% solutions of wheat arabinoxylan (Megazyme) or 5% suspensions of insoluble pentosan from wheat (WIP, produced as described below), respectively, are made in 0.1M acetate buffer pH 5.5. To 1.5 ml of these substrates 30 µl of the following enzyme solutions (final concentration) are added: Xylanase I (0.1 mg/ml), Xylanase II (0.1 mg/ml) and Xylanase III (0.07 mg/ml).

Incubations are carried out at 30° C. for 0, 10, 30, 60 and 120 minutes before heat-inactivation at 95° C. for 20 min. Centrifugation is carried out and supernatants are analysed by injection into three TSK-columns in a row (PW G4000, PW G3000, PW G2500) and saccharides are eluted with 0.4M acetate buffer pH 3.0 at 0.8 ml/min. Eluting saccharides are determined by a Shimadzu RI detector and data are collected and processed by Dionex software. Dextrans (from Serva) are used as molecular weight standards. Collection of data is commenced 15 minutes after injection.

Production of Insoluble Pentosan (WIP) from Wheat Flour 150 kg of common wheat flour was suspended in 450 kg of cold water. The suspension was heated to 60° C. and 600 g of Termamyl 120L® were added. After heating to 95° C. resulting in gelatinization of the starch fraction, the suspension was cooled to 60° C. with continued hydrolysis for 180 min. After adjusting the pH to 8.0 using NaOH 300 g of Alcalase 2.4L® were added. During hydrolysis of protein under constant stirring, the pH was maintained between 7.5 and 8.0 titrating with NaOH. The hydrolysis was continued for 120 min. the precipitate was recovered after centrifugation, washed with water once and then further washed on a 35 µm sieve with cold water to remove all residual soluble material. To the resulting insoluble material up to 20 l of water was added, heated to 60° C. and after an adjustment of the pH to 8.0 with NaOH 100 g of Alcalase 2.4L® were added. The hydrolysis and NaOH-titration were continued until no further drop in pH was observed. The material was then washed again on a 35 µm sieve until all soluble material was removed and, finally, freeze dried.

Determination of FXU (endo-xylanase activity)

The endo-xylanase activity is determined by an assay, in which the xylanase sample is incubated with a remazol-xylan substrate (4-O-methyl-D-glucurono-D-xylan dyed with Remazol Brilliant Blue R, Fluka), pH 6.0. The incubation is performed at 50° C. for 30 min. The background of non-degraded dyed substrate is precipitated by ethanol. The remaining blue colour in the supernatant is determined spectrophotometrically at 585 nm and is proportional to the endoxylanase activity. The endoxylanase activity of the sample is determined relatively to an enzyme standard. The assay is further described in the publication AF 293.6/1-GB, available upon request from Novo Nordisk A/S, Denmark.

Example 1

A library from A. aculeatus consisting of approx. 1.5×10$^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of plates containing 0.1% AZCL xylan (Megazyme, Australia) was then incubated for 3–5 days at 30° C. to detect for xylanase activity. Positive colonies were identified as colonies surrounded by a blue halo. Alternatively, one set of plates was then incubated for 3–5 days at 30° C. before overlayering with a xylan overlayer gel containing 0.1% AZCL xylan and 1% agarose in a buffer with an appropriate pH. After incubation for 1–2 days at 30° C., positive colonies were identified as colonies surrounded by a blue halo. Surprisingly, it was found that xylanase II yeast colonies degrades 4-methyl-umbelliferyl-α-arabinopyranoside in an overlayer with 0.1M citrate buffer, pH 5.0, and 1% agarose resulting in a fluorescent zone. This is the first report of a xylanase having α-arabinopyranosidase activity.

Cells from enzyme-positive colonies were spread for single colony isolation on agar, and an enzyme-producing single colony was selected for each of the xylanase-producing colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The DNA sequences of the enzyme genes are shown in SEQ ID Nos. 1, 3 and 5, respectively.

Isolation of a CDNA gene for expression in Aspergillus: In order to avoid PCR errors in the gene to be cloned, the CDNA was isolated from the yeast plasmids by standard procedures as described below.

One or more of the xylanase-producing colonies was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 µl 5M KOAC was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into E.coli. by standard procedures. Two E. coli colonies were isolated from each of the transformations and analysed with the restriction enzymes HindIII and XbaI which excised the DNA insert. DNA from one of these clones was retransformed into yeast strain JG169.

The DNA sequences of several of the positive clones were partially determined. The DNA sequences of three distinct xylanases (xyl I, xyl II and xyl III) are shown in SEQ ID Nos. 1, 3 and 5, respectively. The sequences shown in these SEQ ID's comprise a poly-A tail, the position of possible stop codons are indicated in the respective amino acid sequences shown in SEQ ID Nos. 2, 4,and 6

Example 2

Expression of Xylanase

In order to express the genes in Aspergillus, cDNA is isolated from one or more representatives of each family by digestion with HindIII/XbaI or other appropriate restriction enzymes, size fractionation on a gel and purification and subsequently ligated to pHD414, resulting in the plasmids pXY-I, pXY-II and pXY-III. After amplification in E. coli, the plasmids are transformed into A. oryzae or A. niger according to the general procedure described in the Materials and Methods section above.

Test of A. oryzae Transformants

Each of the transformants were inoculated on FG-4 agar in the centre of a Petri dish. After 5 days of incubation at 30° C., 4 mm diameter plugs were removed by means of a corkscrew. The plugs were embedded in a xylan overlayer gel, containing 0.1% AZCL xylan and 1% agarose in a buffer with an appropriate pH, and incubated overnight at 40° C. The xylanase activity was identified as described above. Some of the transformants had halos which were significantly larger than the Aspergillus oryzae background. This demonstrates efficient expression of xylanase in Aspergillus oryzae. The 8 transformants with the highest xylanase activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 µl of each supernatant was applied to 4 mm diameter holes punched out in a 0.1% AZCL xylan overlayer gel (25 ml in a 13 cm diameter Petri dish). The xylanase activity was identified by the formation of a blue halo on incubation.

Subsequently, Xyl I, Xyl II and Xyl III, respectively, were produced by fed batch fermentation of A. oryzae expressing the enzymes as described in Materials and Methods above.

Example 3

Purification of Xylanase I, II & III

Purification of Xylanase I

The culture supernatant from fermentation of Aspergillus oryzae expressing the recombinant enzyme is centrifuged and filtered through a 0.2 µm filter to remove the mycelia. 35–50 ml of the filtered supernatant (30–60 mg xylanase I) is ultrafiltrated in a Filtron ultracette or Amicon ultrafiltration device with a 10 kDa membrane to achieve 10 fold concentration. This concentrate is diluted 100 times in 25 mM Tris pH 8.0 in two successive rounds of ultrafiltration in the same device. This ultrafiltratred sample is loaded at 1.5 ml/min on a Pharmacia HR16/20 Fast Flow Q Sepharose anion exchanger equilibrated in 25 mM Tris pH 8.0. After the sample has been applied, the column is washed with two column volumes 25 mM Tris pH 8.0, and bound proteins are eluted with a linear increasing NaCl gradient from 0 to 0.5M NaCl in 25 mM Tris pH 8.0. Xylanase I is not bound to the column and is thus present in the wash fraction. The majority of all impurities are bound to the column, and thus Xylanase I from the run-through/wash fraction is more than 95% pure.

Purification of Xylanase II

The culture supernatant from fermentation of Aspergillus oryzae expressing the recombinant enzyme is centrifuged and filtered through a 0.2 µm filter to remove the mycelia. 35–50 ml of the filtered supernatant (30–60 mg xylanase II) is ultrafiltrated in a Filtron ultracette or Amicon ultrafiltration device with a 10 kDa membrane to achieve 10 fold concentration. This concentrate is diluted 100 times in 20 mM Tris pH 8.0 in two successive rounds of ultrafiltration in the same device. This ultrafiltratred sample is loaded at 1.5 ml/min on a Pharmacia HR16/20 Fast Flow Q Sepharose anion exchanger equilibrated in 20 mM Tris pH 8.0. After the sample has been applied, the column is washed with two column volumes 20 mM Tris pH 8.0, and bound proteins are eluted with a linear increasing NaCl gradient from 0 to 0.6M NaCl in 20 mM Tris pH 8.0. Xylanase II elutes in two distinct peaks at approximately 0.2 & 0.3M NaCl. The enzyme in these two fractions has slightly different isoelectric points (pI 4.65 and pI 4.5 for the first and last eluted peak respectively), but no differences in the enzymatic properties were observed between the two fractions of xylanase II.

Purification of Xylanase III

The culture supernatant from fermentation of *Aspergillus oryzae* expressing the recombinant enzyme is centrifuged and filtered through a 0.2 μm filter to remove the mycelia. 35–50 ml of the filtered supernatant (30–60 mg xylanase III) is ultrafiltrated in a Filtron ultracette or Amicon ultrafiltration device with a 10 kDa membrane to achieve 10 fold concentration. This concentrate is diluted 100 times in 25 mM Tris pH 8.0 in two successive rounds of ultrafiltration in the same device. This ultrafiltratred sample is loaded at 1.5 ml/min on a Pharmacia HR16/20 Fast Flow Q Sepharose anion exchanger equilibrated in 25 mM Tris pH 8.0. After the sample has been applied, the column is washed with two column volumes 25 mM Tris pH 8.0, and bound proteins are eluted with a linear increasing NaCl gradient from 0 to 0.6M NaCl in 25 mM Tris pH 8.0. Xylanase III in this fraction is not completely pure. Thus, the xylanase III containing fractions were concentrated by ultrafiltration in Amicon ultrafiltration device with a 10 kDa membrane to a volume of 4.5 ml and applied to a HR 26/60 Sephacryl S200 gelfiltration column in 0.25M ammonium acetate pH 5.5 at a constant flow of 1 ml/min. Xylanase III is eluted as one distinct peak with a purity of more than 95%.

Example 4

Characterization of Xylanases I, II, III

The xylanases were characterized as described in Materials and Methods and the main results are shown in Table 1.

TABLE 1

|  | Xyl I | Xyl II | Xyl III |
|---|---|---|---|
| Mw | 32.3 | 56 | 24.8 |
| pI | 8.82 | 4.5–4.7 | 5.7 |
| Km | 0.32–0.48 | 0.02–0.10 | 0.01–0.08 |
| Specific activity | 147–170 | 180–204 | 61–69 |

Mw was determined by SDS-PAGE.

pH and Temperature Optimum

The pH optimums of the different enzymes can be seen in FIGS. 3 and 4, respectively. It is seen that all the xylanases have a pH optimum in the range from pH 4–6, xylanase II being the most acidic and xylanase I the most alkaline. Xylanase II is characterized by having a high temperature optimum (70° C.) compared to the other enzymes.

The Km and specific activity for xylanase I, II and III were determined as described in the Materials and Methods section above. The standard deviations on 1/Vmax and Km/Vmax obtained from the linear regression analysis were used to calculate the intervals for the enzymes apparent from the above table.

It is apparent that the xylanases have specific activities in the range of 50–250 μmol/min/mg enzyme protein, Xylanase II having the highest activity.

Gelfiltration Analysis

The gelfiltration chromatograms obtained for Xylanase I, II and III, respectively, (using the method disclosed in the Materials and Methods section above) are shown in FIGS. 5–11.

If the degradation profiles are ordered after decreasing extent of degradation of soluble arabinoxylan after 10 minutes of incubation the following order is obtained: Xylanase II, xylanase I and xylanase III.

If on the other hand the amount of solubilized insoluble arabinoxylan (judged from the area of the chromatograms) after 10 minutes is considered the order is: Xylanase I, xylanase III, xylanase II.

Furthermore, the enzymes can be divided into enzymes which continue degradation of xylan and enzymes which stop their degradation after a certain time. On soluble arabinoxylan xylanase II stops, while xylanase II and III continue the degradation (xylanase I creating large amounts of monomer and dimer and xylanase III being more restricted in its degradation pattern).

On soluble arabinoxylan xylanase I does not stop degradation, while xylanase II and xylanase III do. Xylanase II is special in being very slow in attacking the insoluble substrate.

From the results it is suggested that the enzymes are divided into different classes. Xyl2 acts very fast on soluble arabino-xylan and very slow on insoluble arabinoxylan and the degradation stops after a while. Xyl3 is fast in the degradation of insoluble arabinoxylan, but does not degrade the liberated material extensively. Xyl1 is characterized by an extensive degradation of both soluble and insoluble arabinoxylan to oligomers.

Example 5

Viscosity Reduction of Wheat Flour

Different xylanases were tested for their viscosity reducing capability in wheat flour termed Fakta Flour ("Luksus hvedemel", a commercial flour of non-specified type, available from Dagligvaregruppen, DK-7100 Vejle, Denmark). The flour had the composition shown in Table 2.

TABLE 2

| Component (in pct) | Fakta flour |
|---|---|
| Protein | 10.4 |
| Ash | 0.2 |
| Dry substance | 10.5 |
| Composition of carbohydrates (in PCT): | |
| Glucose | 97.7 |
| Arabinose | 1.1 |
| Xylose | 0.9 |
| Galactose | 0.3 |

The xylanases tested were

Spezyme CP available from Genencor, USA a H. insol ens xylanase (produced as described in Example 2 of WO 92/17573

Xylanase I (produced as described in Example 2 and 3)

Xylanase II (produced as described in Example 2 and 3)

The viscosity reduction was measured by the following method:

100 g of flour is weighed precisely. To 120 ml deionized water eld at 35° C. the enzymes mentioned above were added. The enzymes are dosed as follows:

Spezyme CP: 8.5 FXU (corresponding to 3.4 mg protein)

Xylanase I: 28.3 FXU (corresponding to 0.236 mg enzyme protein and 4.2 mg protein)

Xylanase II: 7.5 FXU (corresponding to 0.19 mg enzyme protein and 0.25 mg protein)

*H. insolens xylanase*: 82.2 FXU (corresponding to 2.2 mg enzyme protein and 22.3 mg protein)

A blank sample is used as control (no enzyme added). The flour and water are stirred by hand for 30 sec and then mixed for precisely 30 sec on a blender (Warring, Commercial laboratory blender, Struers, Adjustments OFF 1–7, rotor in bottom (4 blades)) at 7 (maximum speed). It lasts 30 sec to pour the liquid into the measuring tube at the viscometer (Programmable rheometer, model DV-111, Brookfield, Spindel 25, the measuring tube being termostated at 38° C.). The viscosity at 40 rpm is measured every 15th sec for 4 minutes. The specific viscosity expressed as mean viscosity of sample/mean viscosity of blank in percents is used as a measure of the viscosity reduction. The mean viscosity is a mean of the level reached after 60 sec and until the end of measurements.

The lowest relative viscosity was found in using xylanase II. Other xylanases were found to lower the relative viscosity (xylanase I, Spezyme CP) although to a lesser extent. The *H. insolens* xylanase was found to increase the viscosity at this dosage. As an example the above mentioned dosages resulted in specific viscosity of the "Fakta flour" of 69% for xylanase II, 78% for xylanase I, 87% for Spezyme CP and 107% for *H. insolens* xylanase in viscosity percent of blank.

Example 6

Wheat Separation

The wheat separation capacity of the enzymes mentioned in Example 5 were evaluated by a centrifugation test. The test was conducted on the flour mentioned in Example 5.

The flour and water were mixed according to the procedure described in Example 5. After blending 10 ml of the batter was centrifugated (Megafuge 1.0 Heraeus Sepatech) at 4332 g for 5 minutes. The starch was found in the bottom layer, followed by gluten, sludge and the effluent layer at the top. The separation is expressed as an effluent percent. The higher percentage the better separation.

It was confirmed that xylanase II performs best. As an example the effluent of "Fakta flour" was 14% for a blank sample, 21% for Spezyme CP, 22% for xylanase I and 23% for xylanase II.

Example 7

Use of Xylanase II in the Completing Stage of an Ozone Based Bleaching Sequence, Used for Bleaching of a Kraft Pulp for Papermaking Prior to bleaching with oxygen containing oxidative bleaching agents such as ozone and hydrogen peroxide, kraft pulp is treated in a separate stage with a complexing agent e.g. EDTA or DTPA. The aim is to secure that the subsequent oxidative bleaching is selective towards degradation of the lignin in the pulp fibers. The lignin should be oxidized selectively because decomposition of cellulose means loss of fiber strength.

In the complexing stage the concentration of manganese ions bound to organic acid groups in the fibers are removed to a level of approximately 10 ppm. Higher levels of manganese ions would lead to the formation of undesired free radicals with high reactivity on cellulose, thus reducing the selectivity of the bleaching.

Another metal ion present in the pulp, magnesium, is desired to be present in high amounts due to a cellulose protective function. Complexing agents will remove some magnesium but by choosing a pH in the range 5 to 7 the complexing stage will remove less than half of the amount of magnesium initially present.

The temperature should be as high as possible but energy considerations in practice sets an upper limit of 60° C. The optimum for the *A. aculeatus* II xylanase in bleaching of kraft pulp has been determined to be 60° C. and pH 5. This xylanase is therefore particularly well suited for use in a complexing stage.

This example illustrates how treatment with *A. aculeatus* xylanase can be successfully applied in a complexing stage, simultaneously with a complexing agent.

A sample of industrial oxygen-delignified softwood kraft pulp was analyzed and found to contain 75 ppm manganese and 750 ppm magnesium. The kappa no. was determined to 14.5 according to TAPPI procedure T236.

The bleaching was completed in 4 stages as described below:

Stage 1: EDTA/*A.aculeatus* xylanase II (O/Enz)

0.8 kg $H_2SO_4$ and 2 kg EDTA pr. ton oven dry pulp were mixed into the pulp resulting in a pH of 5.0. A. aculeatus xylanase II produced as described in Examples 2 and 3 was then at a dosage of 15.000 FXU per kg oven dry pulp, and the consistency was adjusted to 10% with deionized water. The pulp was incubated 60 minutes at 60° C.

After the treatment the concentration of dissolved lignin was determined as the absorbency at 280 nm of the waterphase (Dence,L: "Methods in lignin Chemistry", Springer 1992). From initially 1.5 units the absorbency had risen to 4.6. After washing the pulp the kappa no. was determined to 13.4. The increase in absorbency and the decrease in kappa no. show that lignin has been successfully removed from the pulp fibers.

The treated pulp was analyzed for metal ions, the final concentrations were 10 ppm manganese and 450 ppm magnesium. This shows that the treatment with EDTA has lead to the desired result, removing most of the manganese and leaving more than half of the magnesium in the pulp.

A reference pulp was treated likewise but without addition of xylanase. This reference pulp had a kappa no. of 14.3 and a content of 8 ppm manganese and 450 ppm magnesium.

Another reference pulp was treated with xylanase without addition of EDTA. From initially 1.4 absorbency units the absorbency had risen to 4.5. After washing the pulp the kappa no. was determined to 13.5. These results are essentially the same as for the pulp treated with both EDTA and xylanase.

These results demonstrate how EDTA and treatment with *A. aculeatus* xylanase II can be carried out at the same time in the same stage without interference.

Stage 2: Ozone (Z)

The EDTA and xylanase treated pulp was adjusted to a pH of 2 and bleached in a low-consistency ozone reactor at 25° C., dosing ozone at a slow rate under vigorous mixing until exactly 8 kg/ton had been consumed. The pulp was then washed with 60° C. water.

Stage 3: Oxvqen and Hydrogenperoxide reinforced extraction ($E_{op}$)

After washing the pulp was transferred to a pressurized alkaline extraction stage where 0.5 % $H_2O_2$ and 2% NaOH were added and the consistency was made up to 10%. The pulp was incubated under 4 atm. oxygen 75 minutes in a pressure stainless steel vessel. The pulp was washed with 60° C. water.

After the wash, the kappa no. was determined to 1.9 compared to 2.8 for the reference pulp treated without xylanase. The lower final kappa number after xylanase pretreatment demonstrates the improved bleachability obtained. The brightness (SCAN C11) were 77% ISO for the enzyme treated pulp and 69% ISO for the reference pulp.

Stage 4: Chlorine Dioxide (D)

To obtain full brightness the pulp was finally bleached with chlorine dioxide. After adjusting the consistency to 10%, a dosage of 14.5 kg active chlorine (or 5.5 kg chlorine dioxide) per ton pulp was added. The pulp was incubated 3 hours at 60° C. and then washed with water at 60° C.

The final brightness was determined to 90.6% ISO compared to 86.9% ISO obtained for pulp treated without enzyme. The effect of the xylanase had thus been a 3.7% ISO increase in final brightness.

To indicate the pulp strength the pulp viscosity of the bleached pulp was determined according to TAPPI T230. The enzyme treated pulp had a viscosity of 20.5 cP, the control treated without xylanase had a viscosity of 19.8 cP. Thus, the EDTA treatment had worked equally well or better with xylanase present.

Example 8

Use of Xylanase in Animal Feed

Broiler chickens were fed for 6 weeks on an experimental diet with and without enzymes. The diet contained 81% wheat in the first 3 weeks of the trial and 84.5% wheat the last 3 weeks. They were divided into 3 treatments; for the first six weeks each treatment included 12 repetitions with 8 broilers in each, the last 3 weeks 6 repetitions with 5 chickens in each. The treatments included a control without enzymes and the following enzymatic treatments: 400 FXU/kg feed Biofeed Plus (BF+) (available from Novo Nordisk A/S) and 400 FXU/kg feed xylanase II. Both enzymes were formulated as CT granulate according to the method described in WO 92/12645. Weight gain and feed consumption was determined and feed conversion ration (FCR) was calculated from 0 to 3 and from 3 to 6 weeks. Furthermore, jejunal and ileal viscosity was determined on a supernatant from the gut contents, using a Brookfield LVTDV-II viscosimeter.

The results are shown in Tables 3–6.

TABLE 3

Production parameters from 0 to 3 weeks.

| | Weight gain/ chick (g) | Feed intake/ chick (g) | Feed conversion (g/g) |
|---|---|---|---|
| Control | 364.55 | 647.04 | 1.78 |
| | | | 100 |
| BF + 400 | 391.88 | 643.68 | 1.64 |
| | | | 92 |
| Xyl. 2 400 | 404.83 | 650.89 | 1.61 |
| | | | 90 |

TABLE 4

Production parameters from 3 to 6 weeks.

| | Weight gain/ chick (g) | Feed intake/ chick (g) | Feed conversion (g/g) % |
|---|---|---|---|
| Control | 835.51 | 1882.44 | 2.22 |
| | | | 100 |
| BF + 400 | 932.24 | 1906.70 | 2.06 |
| | | | 93 |
| Xyl. 2 400 | 1050.08 | 2068.44 | 1.98 |
| | | | 89 |

TABLE 5

Jejunal viscosity at 3 and 6 weeks.

| | 3 weeks | 6 weeks |
|---|---|---|
| Control | 16.51 | 6.31 |
| BF + 400 | 11.24 | 12.96 |
| Xyl. 2 400 | 6.35 | 3.50 |

TABLE 6

Ileal viscosity at 3 and 6 weeks.

| | 3 weeks | 6 weeks |
|---|---|---|
| Control | 40.07 | 20.41 |
| BF + 400 | 18.46 | 16.92 |
| Xyl. 2 400 | 15.65 | 6.27 |

As can be seen from Tables 3 and 4, the FCR is lower in the groups receiving enzymes, both after 3 and 6 weeks. In both cases xylanase II is better than BF+. This is mainly due to a better growth of the animals in this group.

With regard to jejunal viscosity xylanase II gives a lower viscosity compared to both BF+ and control. This is also the case for ileal viscosity. Both the control and xylanase II gives a lower viscosity after 6 weeks than 3 weeks, while this is not the case for BF+. It thus seems that xylanase II works better during the last 3 weeks than BF+, which is also indicated by the relatively lower FCR of Xylanase II compared to BF+ at 6 weeks.

This experiment thus shows that xylanase II gives a better feed conversion than BF+ on the same FXU basis, i.e. that more nutrients are made available with xylanase II. This may partly be due to a lower ileal viscosity in the xylanase II group.

Example 9

Materials and Methods

Enzymes

Lipase A: The *Humicola lanuginosa* lipase described in EP 305 216 and produced by recombinant DNA techniques in *Asperqillus oryzae* as described in EP 305 216. The lipase has a specific activity of 4,452,000 LU/g and a FAU/g of less than 0.6.

Xylanase A: A xylanase produced by the *Humicola insolens* strain DSM 1800 available from the Deutsche Sammlung von Mikroorganismen und Zellkulturen GmbH and further described in EP 507 723.

Fungamyl: A commercial fungal α-amylase preparation available from Novo Nordisk A/S, Denmark.

Pentopan: A commercial xylanase preparation available from Novo Nordisk A/S, Denmark.

LU/g (Lipase Units/g), FAU/g (Fungal alpha-Amylase Units/g) and FXU (xylanase units/g) were determined by the following assays:

LU—Lipase Units

Lipase activity was assayed using glycerine tributyrat as a substrate and gum-arabic as an emulsifier. 1 LU (Lipase Unit) is the amount of enzyme which liberates 1 µmol titratable butyric acid per minute at 30° C., pH 7.0. The lipase activity was assayed by pH-stat using Radiometer titrator VIT90, Radiometer, Copenhagen. Further details of the assay are given in Novo Analytical Method AF 95/5, available on request.

FAU—Fungal alpha-Amylase Units

1 FA-unit (FAU) is the amount of enzyme which at 37° C. and pH 4.7 breaks down 5260 mg of solid starch per hour. Further details of the assay are given in Novo Analytical Method AF 9.1/3, available on request.

FXU—Xylanase Activity

Was determined as described above.

Preparation of Bread

White bread were prepared from the following basic recipe:

| Basic recipe | |
|---|---|
| Flour (Manitoba) | 100% |
| Salt | 1.5% |
| Yeast (fresh) | 5.0% |
| sugar | 1.5% |
| Water | 58% |

The wheat flour was of the type termed "Manitoba" supplied by "Valsemøllerne", Denmark, October 1993.
Procedure
1. Dough mixing (Spiral mixer)
   2 min. at 700 RPM
   7 min. at 1400 RPM
the mixing time was determined and adjusted by a skilled baker so as to obtain an optimum dough consistence under the testing conditions used.
2. 1st proof: 30° C. - 80% RH, 16 min.
3. Scaling and shaping;
4. Final proof: 32° C. - 80% RH, 35 min.;
5. Baking: 225° C., 20 min. for rolls and 30 min for loaf.

Evaluation of Dough and Baked Products
Properties of the dough and baked products were determined as follows:

Roll specific volume: the volume of 20 rolls are measured using the traditional rape seed method. The specific volume is calculated as volume ml per g bread. The specific volume of the control (without enzyme) is defined as 100. The relative specific volume index is calculated as:

$$\text{Specific vol. index} = \frac{\text{specific volume of 20 rolls}}{\text{specific volume of 20 control rolls}} - *100$$

Loaf specific volume: the mean value of 4 loaves volume are measured using the same methods as described above.

The dough stickiness and crumb structure are evaluated visually according to the following scale:

| Dough stickiness: | almost liquid | 1 |
|---|---|---|
| | too sticky | 2 |
| | slightly sticky | 3 |

| | nice soft | 3.5 |
|---|---|---|
| | normal | 4 |
| | dry | 5 |
| Crumb structure: | very poor | 1 |
| | poor | 2 |
| | non-uniform | 3 |
| | uniform/good | 4 |
| | very good | 5 |

The softness of bread crumb is measured by a SMS-Texture Analyzer. A plunger with a diameter of 20 mm is pressed on the middle of a 20 mm thick slice of bread, The force needed for the plunger to depress the crumb 5 mm with a speed of 2.0 mm/s is recorded and it is expressed as the crumb firmness. The lower the value, the softer is the crumb. Four slices of each bread are measured and the mean value is used.

Xylanase I
The enzyme used was xylanase I, a recombinant A. aculeatus xylanase produced in A. oryzae as described in Examples 2 and 3 above. The effect of this xylanase was compared to xylanase A from H. insolens and a commercial available pentosanase, Pentopan. The enzymes were added either directly into the baking ingredients mix or it was dispersed in water before being added to the mix. All tests were carried out in at least duplicate and the average results were used. The results obtained are shown in Table 7.

It is apparent from Table 5 that the addition of xylanase I increases the volume of rolls or/and loaves significantly and is the effect is larger than that obtained by the prior art xylanase A and Pentopan. At the optimum dosage, i.e. the dosage that gives the maximum specific volume increase without getting a too sticky dough, of the known pentosanase (Pentopan) and xylanase (xylanase A) the max. volume increase is about 10–16%. At the optimum dosage of Xylanase I (about 350–750 FXU per kg flour) a volume increasing of 29–41% can be achieved without causing a too sticky dough. With a longer proofing time at 80% RH and 32° C. an even higher volume increase can be achieved. Furthermore, the crumb structure and crumb softness upon storage are also improved.

TABLE 7

| FXU/kg flour | | 25 | 50 | 100 | 122 | 200 | 350 | 427 | 500 | 750 | 1000 | 0 |
|---|---|---|---|---|---|---|---|---|---|---|---|---|
| Xylanase I | Dough stickiness | 4 | 4 | 3.5 | | 3.5 | 3.5 | | 3.5 | 3 | 2.5 | 4 |
| Xylanase I | SP Volume index/-Rolls | 103 | 109 | 111 | | 119 | 121 | | 129 | 141 | 133 | 100 |
| Xylanase I | SP Volume index/-/Loaves* | 101 | 102 | 105 | | 110 | 110 | | 114 | 122 | 121 | 100 |
| Xylanase I | SP Volume index/-Loaves** | | | | | | 134 | | | | | |
| | Crumb structure | | 3 | 3.5 | | 3.5 | 3.5 | | 4 | | | 3 |
| | Crumb firmness | | 0.278 | 0.282 | | 0.206 | 0.258 | | 0.169 | 0.173 | 0.189 | 0.399 |
| | Day 4 | | 0.434 | 0.440 | | 0.345 | 0.346 | | 0.357 | 0.320 | 0.348 | 0.509 |
| | Day 7 | | 0.589 | 0.551 | | 0.451 | 0.561 | | 0.376 | 0.383 | 0.380 | 0.658 |
| Xylanase A | Dough stickiness | | 3.5 | 3 | | | | | | | | |
| | SP Volume index/-Rolls | | 108 | 116 | | | | | | | | |
| Pentopan | Dough stickiness | | | | | 3.5 | | 3 | | | | |
| | SP Volume index/-Rolls | | | | | 106 | | 111 | | | | |

*low fermentation time: 35 min.
**longer fermentation time: 50 min.

Example 10

In the same manner as described in Example 9, baking trials with xylanase II, a recombinant A. aculeatus xylanase produced as described in Annex 1, xylanase A and Pentopan were performed. The results obtained are shown from Table 8.

TABLE 8

| FXU/kg flour | | 25 | 50 | 100 | 122 | 200 | 350 | 427 | 500 | 0 |
|---|---|---|---|---|---|---|---|---|---|---|
| Xylanase II | Dough stickiness | 4 | 4 | 3.5 | | 3–3.5 | 2.5–3 | | 2.5 | |
| | SP Volume index/Rolls | 111 | 113 | 123 | | 124 | 126 | | 134 | |
| | SP Volume index/loaves | 103 | 107 | 109 | | 113 | 117 | | 117 | |
| | Crumb structure | 3 | 3.5 | 4 | | 4 | 4.5 | | 4.5 | 3 |
| | Crumb firmness day 1 | | 0.227 | 0.193 | | 0.209 | 0.176 | | 0.215 | 0.399 |
| | Day 4 | | 0.362 | 0.359 | | 0.358 | 0.289 | | 0.294 | 0.509 |
| | Day 7 | | 0.435 | 0.390 | | 0.433 | 0.398 | | 0.386 | 0.658 |
| Xylanase A | Dough stickiness | | 3.5 | 3 | | | | | | |
| | SP Volume index/Rolls | | 108 | 116 | | | | | | |
| Pentopan | Dough stickiness | | | | 3.5 | | | 3 | | |
| | SP Volume index/Rolls | | | | 106 | | | 111 | | |

*low fermentation time: 35 min.

It is apparent from Table 8 that the use of xylanase II increases the volume of rolls or/and loaves significantly and the effect is larger than the prior art xylanase and pentosanase. At the optimum dosage of Xylanase II (i.e. about 200 FXU per kg flour) a volume increasing of 24% is achieved without causing a too sticky dough. Furthermore, the crumb structure and crumb softness upon storage are also improved.

REFERENCES

Aviv, H. & Leder, P. 1972. Proc. Natl. Acad. Sci. U. S. A. 69: 1408–1412.

Axelsen N. et al. in: *A Manual of Ouantitative Immunoelectrophoresis*, Blackwell Scientific Publications, 1973, Chapter 23.

Becker, D. M. & Guarante, L. 1991. Methods Enzymol. 194: 182–187.

Bedford et al., Proceedings of the 1st Symposium on Enzymes in Animal Nutrition, 1993, pp. 73–77.

Blackwell Scientific Publications, 1967, pp. 655–706.

Chirgwin, J. M., Przybyla, A. E., MacDonald, R. J. & Rutter, W. J. 1979. Biochemistry 18: 5294–5299.

Detroym R. W. In: Organic Chemicals from Biomass, (CRC Press, Boca Raton, Fla, 1981) 19–41.

Eriksson, K. E. L., Wood Science and Technology 24 (1990): 79–101.

Fournier, R. et al., Biotech. and Bioeng. Vol. XXVII, pp. 539–546, 1985.

Gubler, U. & Hoffman, B. J. 1983. Gene 25: 263–269.

Johnstone A. and Thorpe R., *Immunochemistry in Practice*, Blackwell Scientific Publications, 1982 (more specifically pp. 27–31.

Ouchterlony O. in: *Handbook of Experimental Immunolooy* (D. M. Weir, Ed.).

Paice, et al., Biotechnol. and Bioeng. 32 (1988): 235–239.

Paice, M. G., and L. Jurasek., J. Wood Chem. Technol. 4: 187–198.

Pommier et al., Tappi Journal (1989): 187–191).

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U. S. A. 74: 5463–5467.

Senior, D. J., et al., Biotechnol. Letters 10 (1988):907–912].

Shei, J. C., et al., Biotech. and Bioeng. Vol. XXVII, pp. 533–538, 1985.

Visser, J. et al., Progress in Biotechnology 7, Proceedings of an Int. Symposium in Wageningen, The Netherlands, Dec. 8–11, 1991, publ. by Elsevier, 1992.

Visser et al., in "Xylans and Xylanases", Elsevier Science Publishers, 1991.

Vietor et al., 1993, J. Inst. Brew., May–June, 99, pp. 243–248.

What is claimed is:

1. A DNA construct which comprises a DNA sequence encoding an enzyme having xylanase activity as measured by release of reducing sugars from birch xylan or by release of blue color from AZCL-birch xylan, and which DNA sequence hybridizes to a DNA depicted in SEQ ID NO. 5 under the following conditions: hybridizing in 5× SSC, 5× Denhardt's solution, 0.5% SDS and 100 μg/ml salmon sperm DNA for 16 hrs. at about 65° C. followed by washes in 5× SSC at 65° C., 2× SSC, 0.5% SDS, 0.2× SSC, 0.5% SDS and 5× SSC.

2. The DNA construct of claim 1, in which the enzyme encoded by the DNA sequence is derived from an Aspergillus species.

3. The DNA construct of claim 1, in which the enzyme encoded by the DNA sequence is derived from *Aspergillus aculeatus*.

4. The DNA construct of claim 1, in which the DNA sequence is isolated from a DNA library of *Aspergillus aculeatus*, CBS 101.43.

5. A recombinant expression vector comprising the DNA construct of claim 1.

6. A cell comprising the recombinant expression vector of claim 5.

7. The cell according to claim 6, in which the cell is a eukaryotic cell.

8. The cell according to claim 6, in which the cell is a fUngal cell.

9. The cell according to claim 6, in which the cell is a yeast cell or filamentous fungal cell.

10. The cell according to claim 6, in which the cell belongs to a strain of Aspergillus.

11. The cell according to claim 6, in which the cell belongs to a strain of *Aspergillus niger* or *Aspergillus oryzae*.

12. A method for producing an enzyme exhibiting xylanase activity comprising culturing the cell of claim 6 under conditions permitting the production of the enzyme and recovering the enzyme from the culture.

13. A DNA construct which comprises a DNA sequence encoding an enzyme having sylanase activity depicted in SEQ ID NO:6 or mutant thereof having the same xylanase activity as the xylanase depicted in SEQ ID NO. 6 as measured by release of reducing sugars from birch xylan or by release of blue color from AZCL-birch xylan, said said mutant also having a pH optimum of 5–6 and a temperature optimum of 40°–50° C.

14. The DNA construct of claim 13, in which the enzyme encoded by the DNA sequence is derived from an Aspergillus species.

15. The DNA construct of claim 13, in which the enzyme encoded by the DNA sequence is derived from *Aspergillus aculeatus*.

16. The DNA construct of claim 13, in which the DNA sequence is isolated from a DNA library of *Aspergillus aculeatus*, CBS 101.43.

17. A recombinant expression vector comprising the DNA construct of claim 13.

18. A cell comprising the recombinant expression vector of claim 17.

19. The cell according to claim 18, in which the cell is a eukaryotic cell.

20. The cell according to claim 19, in which the cell is a fungal cell.

21. The cell according to claim 19, in which the cell is a yeast cell or filamentous fungal cell.

22. The cell according to claim 19, in which the cell belongs to a strain of Aspergilus.

23. The cell according to claim 19, in which the cell belongs to a strain of *Aspergillus niger* or *Aspergillus oryzae*.

24. A method for producing an enzyme exhibiting xylanase activity comprising culturing the cell of claim 19 under conditions permitting the production of the enzyme and recovering the enzyme from the culture.

25. A DNA construct which comprises a DNA sequence derived from *Aspergillus aculeatus* encoding an enzyme having xylanase activity as measured by release of reducing sugars from birch xylan or by release of blue color from AZCL-birch xylan, said enzyme having a pH optimum of 4–5 and at a temperature range of 70°–80° C. and in which said enzyme is encoded by a DNA sequence comprising the partial DNA sequence depicted in SEQ ID NO. 41.

26. The DNA construct of claim 25, in which the DNA sequence is isolated from a DNA library of *Aspergillus aculeatus*, CBS 101.43.

27. A recombinant expression vector comprising the DNA construct of claim 25.

28. A cell comprising the recombinant expression vector of claim 27.

29. The cell according to claim 28, in which the cell is a eukaryotic cell.

30. The cell according to claim 28, in which the cell is a fungal cell.

31. The cell according to claim 28, in which the cell is a yeast cell or filamentous fungal cell.

32. The cell according to claim 28, in which the cell belongs to a strain of Aspergillus.

33. The cell according to claim 28, in which the cell belongs to a strain of *Aspergillus niger* or *Aspergillus oryzae*.

34. A method for producing an enzyme exhibiting xylanase activity comprising culturing the cell of claim 28 under conditions permitting the production of the enzyme and recovering the enzyme from the culture.

35. A DNA construct which comprises a DNA sequence derived from *Aspergillus aculeatus* encoding an enzyme having xylanase activity as measured by release of reducing sugars from birch xylan or by release of blue color from AZCL-birch xylan, said enzyme having a pH optimum of 5–6 and at a temperature range of 40°–50° C. and in which said enzyme is encoded by a DNA sequence comprising the partial DNA sequence depicted in SEQ ID NO. 42.

36. The DNA construct of claim 35, in which the DNA sequence is isolated from a DNA library of *Aspergillus aculeatus*, CBS 101.43.

37. A recombinant expression vector comprising the DNA construct of claim 35.

38. A cell comprising the recombinant expression vector of claim 37.

39. The cell according to claim 38, in which the cell is a eukaryotic cell.

40. The cell according to claim 38, in which the cell is a fungal cell.

41. The cell according to claim 38, in which the cell is a yeast cell or filamentous fungal cell.

42. The cell according to claim 38, in which the cell belongs to a strain of Aspergillus.

43. The cell according to claim 38, in which the cell belongs to a strain of *Aspergillus niger* or *Aspergillus oryzae*.

44. A method for producing an enzyme exhibiting xylanase activity comprising culturing the cell of claim 38 under conditions permitting the production of the enzyme and recovering the enzyme from the culture.

* * * * *

UNITED STATES PATENT AND TRADEMARK OFFICE
CERTIFICATE OF CORRECTION

PATENT NO. : 5,885,819
DATED : March 23, 1999
INVENTOR(S) : Kofod et al.

It is certified that error appears in the above-identified patent and that said Letters Patent is hereby corrected as shown below:

Col. 57, line 33, claim 8, delete "fUngal" and insert --fungal--

Signed and Sealed this

Fourteenth Day of March, 2000

Attest:

Q. TODD DICKINSON

*Attesting Officer*   *Commissioner of Patents and Trademarks*